United States Patent
Okada et al.

(10) Patent No.: US 9,562,158 B2
(45) Date of Patent: Feb. 7, 2017

(54) SILICONE RUBBER-BASED HARDENING RESIN COMPOSITION, MOLDED ARTICLE, AND MEDICAL TUBE

(71) Applicant: SUMITOMO BAKELITE COMPANY LIMITED, Shinagawa-ku (JP)

(72) Inventors: Jun Okada, Tokyo (JP); Kazunobu Senoo, Tokyo (JP)

(73) Assignee: SUMITOMO BAKELITE COMPANY LIMITED, Shinagawa-ku (JP)

( * ) Notice: Subject to any disclaimer, the term of this patent is extended or adjusted under 35 U.S.C. 154(b) by 0 days.

(21) Appl. No.: 14/879,685

(22) Filed: Oct. 9, 2015

(65) Prior Publication Data

US 2016/0032101 A1 Feb. 4, 2016

Related U.S. Application Data

(63) Continuation-in-part of application No. 14/001,093, filed as application No. PCT/JP2012/054250 on Feb. 22, 2012, now abandoned.

(30) Foreign Application Priority Data

Feb. 23, 2011 (JP) ................. 2011-037516
Feb. 23, 2011 (JP) ................. 2011-037513

(51) Int. Cl.
| C08L 83/04 | (2006.01) |
|---|---|
| A61L 29/06 | (2006.01) |
| A61L 29/04 | (2006.01) |
| C08K 9/06 | (2006.01) |
| A61L 29/12 | (2006.01) |
| C08K 3/36 | (2006.01) |
| C08G 77/20 | (2006.01) |
| C08G 77/12 | (2006.01) |

(52) U.S. Cl.
CPC .............. *C08L 83/04* (2013.01); *A61L 29/049* (2013.01); *A61L 29/126* (2013.01); *C08K 9/06* (2013.01); *C08G 77/12* (2013.01); *C08G 77/20* (2013.01); *C08K 3/36* (2013.01); *C08L 2203/02* (2013.01)

(58) Field of Classification Search
None
See application file for complete search history.

(56) References Cited

U.S. PATENT DOCUMENTS

| 3,671,480 A | 6/1972 | Wada et al. |
|---|---|---|
| 3,884,866 A | 5/1975 | Jeram et al. |
| 4,061,609 A | 12/1977 | Bobear |
| 4,340,709 A | 7/1982 | Jeram et al. |
| 4,539,357 A | 9/1985 | Bobear |
| 4,753,978 A | 6/1988 | Jensen |
| 4,788,001 A | 11/1988 | Narula |
| 5,008,305 A * | 4/1991 | Kennan ............... C09C 1/3081 106/490 |
| 5,179,148 A | 1/1993 | Inoue et al. |
| 5,548,006 A | 8/1996 | Hirabayashi et al. |
| 5,679,727 A | 10/1997 | Griffith et al. |
| 5,700,853 A | 12/1997 | Yoshida et al. |
| 5,948,539 A | 9/1999 | Paulsen et al. |
| 5,998,516 A * | 12/1999 | Burkus, II ............... C08K 5/19 524/104 |
| 6,040,369 A | 3/2000 | Paulsen et al. |
| 6,331,588 B1 | 12/2001 | Azechi et al. |
| 8,338,528 B2 * | 12/2012 | Scholz ..................... C08K 9/04 524/588 |
| 2003/0130363 A1 | 7/2003 | Meguriya |
| 2003/0232202 A1 | 12/2003 | Yaginuma et al. |
| 2005/0277725 A1 | 12/2005 | Ikeno et al. |
| 2006/0188733 A1 | 8/2006 | Achenbach et al. |
| 2011/0039991 A1 | 2/2011 | Iijima et al. |
| 2014/0242312 A1 | 8/2014 | Murai et al. |

FOREIGN PATENT DOCUMENTS

| JP | 7-228782 | 8/1995 |
|---|---|---|
| JP | 7-258551 | 10/1995 |
| JP | 7-331079 | 12/1995 |
| JP | 8-269339 | * 10/1996 |
| JP | 8-323857 | 12/1996 |
| JP | 2001-500306 | 1/2001 |
| JP | 2005-68273 | 3/2005 |
| JP | 2006-1953 | 1/2006 |
| JP | 2006-1954 | 1/2006 |
| JP | 2009-173837 | 8/2006 |
| JP | 2006-233215 | 9/2006 |
| JP | 2007-526373 | 9/2007 |
| JP | 2010-13495 | 1/2010 |
| JP | 2011-162714 | 8/2011 |
| JP | 2012-12448 | 1/2012 |
| JP | 2012-36288 | 2/2012 |
| JP | 2012-46656 | 3/2012 |
| JP | 4917184 B1 | 4/2012 |
| WO | WO 98/10433 | 3/1998 |
| WO | WO 2005/095503 A1 | 10/2005 |

OTHER PUBLICATIONS

International Search Report issued May 29, 2012 in Application No. PCT/JP2012/054250 (With English Translation).
Extended European Search Report issued Jul. 17, 2014 in Patent Application No. 12750080.9.
"Silicones: An Introduction to Their Chemistry and Applications" © 1962 Chapel River Press Ltd.

* cited by examiner

*Primary Examiner* — Marc Zimmer
(74) *Attorney, Agent, or Firm* — Oblon, McClelland, Maier & Neustadt, L.L.P.

(57) ABSTRACT

A silicone rubber-based hardening composition includes a linear organopolysiloxane having a vinyl group (A), an organohydrogen polysiloxane (B), and a silica filler (C) of which surface is treated with a silane coupling agent having a trimethylsilyl group. The linear organopolysiloxane having a vinyl group (A) includes a first linear organopolysiloxane having a vinyl group (A1), and a second linear organopolysiloxane having a vinyl group (A2).

20 Claims, No Drawings

SILICONE RUBBER-BASED HARDENING RESIN COMPOSITION, MOLDED ARTICLE, AND MEDICAL TUBE

CROSS REFERENCES TO RELATED APPLICATIONS

This application is a continuation-in-part of U.S. patent application Ser. No. 14/001,093, filed Aug. 22, 2013, which is the National Stage of the International Patent Application No. PCT/JP12/54250, filed Feb. 22, 2012. This application claims priority to Japanese application Nos. JP 2011-037513, filed Feb. 23, 2011, and JP 2011-037516, filed Feb. 23, 2011. The disclosures of all of the above applications are incorporated herein by reference in their entireties.

TECHNICAL FIELD

The present invention relates to a silicone rubber-based hardening resin composition, a molded article using the silicone rubber-based hardening resin composition, and a medical tube using the molded article.

BACKGROUND ART

Since silicone rubber is excellent in heat resistance, flame resistance, chemical stability, weather resistance, radiation resistance, electrical properties, and the like, it has been used for a variety of uses in a wide range of areas. In particular, since silicone rubber is physiologically inactive and reacts little with body tissues when the silicone rubber is in touch with a living body, it has been used as a material for medical instruments such as medical catheters.

The medical catheter is a tube which is inserted into a body cavity such as a thoracic cavity and an abdominal cavity, a lumen such as an alimentary canal and a ureter, and a blood vessel, and used to discharge a body fluid, or injecting or dripping a drug solution, nutrition, or a contrast medium. The medical catheter is required to have scratch resistance (tear resistance), kink resistance (tensile strength), transparency, flexibility (tensile elongation properties), and the like, in addition to biocompatibility. Specifically, the medical catheter is used as a drainage tube of an aspirator for removing an effluent such as blood, and pus after a surgery operation, and a tube for intaking nutrient after a surgical operation such as percutaneous endoscopic gastrostomy (PEG). In addition, in order to make silicone rubber for an extremely fine tube as a catheter, the silicone rubber composition, which is a raw material of the silicone rubber, is required to have extrusion molding properties.

As a material for medical catheters, soft polyvinyl chloride is also widely used in addition to silicone rubber. Compared with polyvinyl chloride, silicone rubber is excellent in biocompatibility and flexibility, but required to have improved strength such as tear resistance, and tensile strength, in particular, tear resistance. When the tear resistance is insufficient, the catheter may be torn by the damage made by a needle or a blade used during a surgical operation. When the tensile strength is insufficient, the catheter may be bent and closed (kinked), and thereby, a flow of a body fluid which should be discharged or a drug solution which should be injected may be stagnated.

Therefore, in order to improve the tear strength and tensile strength of silicone rubber, various methods have been suggested (for example, Patent Documents Nos. 1 to 8).

For example, Patent Document No. 1 discloses a hardening silicone rubber composition which contains mainly organopolysiloxane having high viscosity and containing a small amount of a vinyl group (crude rubber (A)), and is added with organopolysiloxane having low viscosity and containing a large amount of a vinyl group (silicone oil (B)), an organopolysiloxane copolymer containing a vinyl group (silicone resin containing a vinyl group (C)), organo-hydrogen siloxane (crosslinking agent (D)), platinum or a platinum compound (hardening catalyst (E)), and fine powdered silica (filler (F)).

PRIOR ART DOCUMENT

Patent Document

Patent Document No. 1: Japanese Unexamined Patent Application, First Publication No. Hei 7-331079
Patent Document No. 2: Japanese Unexamined Patent Application, First Publication No. Hei 7-228782
Patent Document No. 3: Japanese Unexamined Patent Application, First Publication No. Hei 7-258551
Patent Document No. 4: U.S. Pat. No. 3,884,866
Patent Document No. 5: U.S. Pat. No. 4,539,357
Patent Document No. 6: U.S. Pat. No. 4,061,609
Patent Document No. 7: U.S. Pat. No. 3,671,480
Patent Document No. 8: Japanese Unexamined Patent Application, First Publication No. 2005-68273

DISCLOSURE OF THE INVENTION

Problems to be Solved

Examples of a method for applying high tear resistance to silicone rubber include addition of an inorganic filler such as silica fine particles, and changing the crosslinking density (distributing an area at which the crosslinking density is high and an area at which the crosslinking density is low in the silicone rubber). In a method for improving the tear strength by changing the crosslinking density, it is believed that the area at which the crosslinking density is high resists the tear stress.

However, the mechanical strength, in particular, the tear strength of the silicone rubber is desired to be further improved.

In addition, as a material for the medical catheter, the silicone rubber is desired to have a certain level of hardness. When the catheter made of a material having low hardness is inserted into a target part (for example, thoracic cavity), the catheter is easily deformed due to insertion resistance, this means "no elasticity", and easily closed due to low kink resistance.

As explained above, the mechanical strength of the silicone rubber is desired to be improved. In particular, the silicone rubber excellent in tear strength and hardness is desired to be developed.

In consideration of the above-described problems, it is an object of the present invention is to provide a silicone rubber-based hardening composition which can produce a silicone rubber having excellent tear strength.

In addition, another object of the present invention is to provide a silicone rubber-based hardening composition which can produce a silicone rubber having excellent tensile strength, tear strength, and hardness.

Means for Solving the Problem

The object is achieved by the following inventions (1) to (32).

(1) A silicone rubber-based hardening composition containing:
linear organopolysiloxane having a vinyl group (A);
organohydrogen polysiloxane (B); and
silica filler (C) of which the surface is treated with a silane coupling agent having a trimethylsilyl group, wherein the linear organopolysiloxane having a vinyl group (A) includes a first linear organopolysiloxane having a vinyl group (A1), and a second linear organopolysiloxane having a vinyl group (A2).

(2) The silicone rubber-based hardening composition according to (1), wherein the linear organopolysiloxane having a vinyl group (A) is represented by the following formula (1).

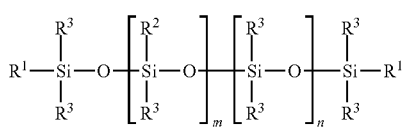

(1)

(in the formula (1), m denotes an integer from 1 to 1,000; n denotes an integer from 3,000 to 10,000; $R^1$ denotes an alkyl group, alkenyl group, aryl group, which contains 1 to 10 carbon atoms, and has a substituted group or no substituted group, or a hydrocarbon group in which these groups are combined; $R^2$ denotes an alkyl group, alkenyl group, aryl group, which contains 1 to 10 carbon atoms, and has a substituted group or no substituted group, or a hydrocarbon group in which these groups are combined; $R^3$ denotes an alkyl group, aryl group, which contains 1 to 8 carbon atoms, and has a substituted group or no substituted group, or a hydrocarbon group in which these groups are combined; and at least one of plural $R^1$ and $R^2$ is an alkenyl group.)

(3) The silicone rubber-based hardening composition according to (1) or (2), wherein the organohydrogen polysiloxane (B) is a linear organohydrogen polysiloxane represented by the following formula (2).

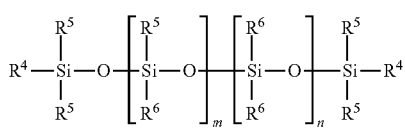

(2)

(in the formula (2), m denotes an integer from 2 to 500; n denotes an integer from 2 to 400; m and n satisfy 20≤(m+n)≤500; $R^4$ denotes an alkyl group, alkenyl group, aryl group, which contains 1 to 10 carbon atoms, and has a substituted group or no substituted group, a hydrocarbon group in which these groups are combined, or a hydride group; $R^5$ denotes an alkyl group, alkenyl group, aryl group, which contains 1 to 10 carbon atoms, and has a substituted group or no substituted group, a hydrocarbon group in which these groups are combined, or a hydride group; at least two of plural $R^4$ and $R^5$ are a hydride group; and $R^6$ denotes an alkyl group, aryl group, which contains 1 to 8 carbon atoms, and has a substituted group or no substituted group, or a hydrocarbon group in which these groups are combined.)

(4) The silicone rubber-based hardening composition according to any one of (1) to (3), wherein the silane coupling agent having a trimethylsilyl group is at least one selected from the group consisting of silazane, chlorosilane, and alkoxysilane.

(5) The silicone rubber-based hardening composition according to any one of (1) to (4), wherein the silane coupling agent having a trimethylsilyl group is at least one selected from the group consisting of hexamethyldisilazane, trimethylchlorosilane, trimethylmethoxysilane, and trimethylethoxysilane.

(6) The silicone rubber-based hardening composition according to any one of (1) to (5), wherein the silica filler (C) of which the surface is treated with a silane coupling agent having a trimethylsilyl group contains carbon in a range of 0.1% by weight to 7.0% by weight.

(7) The silicone rubber-based hardening composition according to any one of (1) to (6), wherein the silica filler (C) of which the surface is treated with a silane coupling agent having a trimethylsilyl group has a specific surface area in a range of 30 $m^2/g$ to 500 $m^2/g$, and an average primary particle diameter of 100 nm or less.

(8) The silicone rubber-based hardening composition according to any one of (1) to (7), wherein the first linear organopolysiloxane having a vinyl group (A1) contains 0.2% by mole or less of a vinyl group, and the second linear organopolysiloxane having a vinyl group (A2) contains 0.50% by mole to 12% by mole of a vinyl group.

(9) The silicone rubber-based hardening composition according to any one of (1) to (8), wherein the polymerization degree of the linear organopolysiloxane having a vinyl group (A) is in a range of 4,000 to 8,000.

(10) The silicone rubber-based hardening composition according to any one of (1) to (9), wherein the organohydrogen polysiloxane (B) does not have a vinyl group.

(11) The silicone rubber-based hardening composition according to any one of (1) to (10), wherein the silicone rubber-based hardening composition contains 0.1 parts by weight to 10 parts by weight of the organohydrogen polysiloxane (B), and 15 parts by weight to 150 parts by weight of the silica filler (C) of which the surface is treated with a silane coupling agent having a trimethylsilyl group, relative to 100 parts by weight of the linear organopolysiloxane having a vinyl group (A).

(12) The silicone rubber-based hardening composition according to any one of (1) to (11), wherein the silicone rubber-based hardening composition further contains a catalyst quantity of platinum or a platinum compound.

(13) A molded article which is produced using the silicone rubber-based hardening composition according to any one of (1) to (12).

(14) A medical tube which is the molded article according to (13).

(15) A silicone rubber-based hardening composition containing:
linear organopolysiloxane having a vinyl group (A);
organohydrogen polysiloxane (B);
silica filler (C) of which the surface is treated with a silane coupling agent having a trimethylsilyl group; and
silica filler (D) of which the surface is treated with a silane coupling agent having an organosilyl group containing a vinyl group.

(16) The silicone rubber-based hardening composition according to (15), wherein each of the first linear organopolysiloxane having a vinyl group (A1) and the second linear organopolysiloxane having a vinyl group (A2) is represented by the following formula (1).

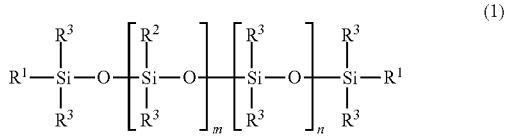 (1)

(in the formula (1), m denotes an integer from 1 to 1,000; n denotes an integer from 3,000 to 10,000; $R^1$ denotes an alkyl group, alkenyl group, aryl group, which contains 1 to 10 carbon atoms, and has a substituted group or no substituted group, or a hydrocarbon group in which these groups are combined; $R^2$ denotes an alkyl group, alkenyl group, aryl group, which contains 1 to 10 carbon atoms, and has a substituted group or no substituted group, or a hydrocarbon group in which these groups are combined; $R^3$ denotes an alkyl group, aryl group, which contains 1 to 8 carbon atoms, and has a substituted group or no substituted group, or a hydrocarbon group in which these groups are combined; and at least one of plural $R^1$ and $R^2$ is an alkenyl group.)

(17) The silicone rubber-based hardening composition according to (15) or (16), wherein the organohydrogen polysiloxane (B) is a linear organohydrogen polysiloxane represented by the following formula (2).

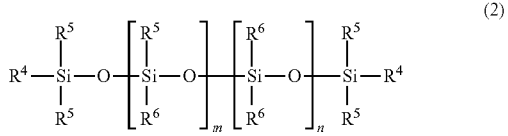 (2)

(in the formula (2), m denotes an integer from 2 to 500; n denotes an integer from 2 to 400; m and n satisfy 20≤(m+n)≤500; $R^4$ denotes an alkyl group, alkenyl group, aryl group, which contains 1 to 10 carbon atoms, and has a substituted group or no substituted group, a hydrocarbon group in which these groups are combined, or a hydride group; $R^5$ denotes an alkyl group, alkenyl group, aryl group, which contains 1 to 10 carbon atoms, and has a substituted group or no substituted group, a hydrocarbon group in which these groups are combined, or a hydride group; at least two of plural $R^4$ and $R^5$ are a hydride group; and $R^6$ denotes an alkyl group, aryl group, which contains 1 to 8 carbon atoms, and has a substituted group or no substituted group, or a hydrocarbon group in which these groups are combined.)

(18) The silicone rubber-based hardening composition according to any one of (15) to (17), wherein the silane coupling agent having a trimethylsilyl group is at least one selected from the group consisting of silazane, chlorosilane, and alkoxysilane.

(19) The silicone rubber-based hardening composition according to any one of (15) to (18), wherein the silane coupling agent having a trimethylsilyl group is at least one selected from the group consisting of hexamethyldisilazane, trimethylchlorosilane, trimethylmethoxysilane, and trimethylethoxysilane.

(20) The silicone rubber-based hardening composition according to any one of (15) to (19), wherein the silica filler (C) of which the surface is treated with a silane coupling agent having a trimethylsilyl group contains carbon in a range of 0.1% by weight to 7.0% by weight.

(21) The silicone rubber-based hardening composition according to any one of (15) to (20), wherein the silica filler (C) of which the surface is treated with a silane coupling agent having a trimethylsilyl group has a specific surface area in a range of 30 $m^2$/g to 500 $m^2$/g, and an average primary particle diameter of 100 nm or less.

(22) The silicone rubber-based hardening composition according to any one of (15) to (21), wherein the silane coupling agent having an organosilyl group containing a vinyl group is at least one selected from the group consisting of silazane, chlorosilane, and alkoxysilane.

(23) The silicone rubber-based hardening composition according to any one of (15) to (22), wherein the silane coupling agent having an organosilyl group containing a vinyl group is at least one selected from the group consisting of methacryloxypropyl triethoxysilane, methacryloxypropyl trimethoxysilane, methacryloxypropyl methyldiethoxysilane, methacryloxypropyl methyldimethoxysilane, divinyl tetramethyldisilazane, vinyltriethoxysilane, vinyltrimethoxysilane, and vinylmethyldimethoxysilane.

(24) The silicone rubber-based hardening composition according to any one of (15) to (23), wherein the silica filler (D) of which the surface is treated with a silane coupling agent having an organosilyl group containing a vinyl group has a specific surface area in a range of 30 $m^2$/g to 500 $m^2$/g, and an average primary particle diameter of 100 nm or less.

(25) The silicone rubber-based hardening composition according to any one of (15) to (24), wherein the linear organopolysiloxane having a vinyl group (A) contains a first linear organopolysiloxane having a vinyl group (A1) containing 0.2% by mole or less of a vinyl group, and a second linear organopolysiloxane having a vinyl group (A2) containing 0.50% by mole to 12% by mole of a vinyl group.

(26) The silicone rubber-based hardening composition according to any one of (15) to (25), wherein the polymerization degree of the linear organopolysiloxane having a vinyl group (A) is in a range of 4,000 to 8,000.

(27) The silicone rubber-based hardening composition according to any one of (15) to (26), wherein the organohydrogen polysiloxane (B) does not have a vinyl group.

(28) The silicone rubber-based hardening composition according to any one of (15) to (27), wherein the silicone rubber-based hardening composition contains 0.1 parts by weight to 10 parts by weight of the organohydrogen polysiloxane (B), 15 parts by weight to 150 parts by weight of the silica filler (C) of which the surface is treated with a silane coupling agent having a trimethylsilyl group, and 0 parts by weight to 40 parts by weight of the silica filler (D) of which the surface is treated with a silane coupling agent having an organosilyl group containing a vinyl group, relative to 100 parts by weight of the linear organopolysiloxane having a vinyl group (A).

(29) The silicone rubber-based hardening composition according to any one of (15) to (28), wherein the silicone rubber-based hardening composition further contains a catalyst quantity of platinum or a platinum compound.

(30) The silicone rubber-based hardening composition according to any one of (15) to (29), wherein the silicone rubber-based hardening composition produces silicone rubber having a type A-durometer hardness after hardening according to JIS K 6253 (2006) of 55 or more.

(31) A molded article which is produced using the silicone rubber-based hardening composition according to any one of (15) to (30).

(32) A medical tube which is produced using the molded article according to (31).

Effects of the Present Invention

The silicone rubber obtained by hardening the silicone rubber-based hardening composition according to the present invention is excellent in mechanical strength such as tensile strength and tear strength, in particular, tear strength. Therefore, the molded article which is obtained by using the silicone rubber-based hardening composition and the medical tube which is obtained by using the molded article have high mechanical strength. In other words, according to the present invention, it is possible to produce a medical catheter made of silicone rubber which is excellent in scratch resistance and kink resistance, in particular, scratch resistance.

In addition, the silicone rubber, which is obtained by hardening the silicone rubber-based hardening composition according to the present invention, is excellent in balance between mechanical strength, in particular, tensile strength, tear strength, and hardness. Therefore, the molded articles made of the silicone rubber-based hardening composition, and the medical tube made of the molded article have high mechanical strength, such as tensile strength, tear strength, and hardness. In other words, according to the present invention, it is possible to produce a medical catheter made of silicone rubber which is excellent in kink resistance, scratch resistance, and ease of insertion.

DESCRIPTION OF EMBODIMENTS

The silicone rubber-based hardening composition according to the present invention contains linear organopolysiloxane having a vinyl group (A), organohydrogen polysiloxane (B), and silica filler (C) of which the surface is treated with a silane coupling agent having a trimethylsilyl group.

In order to improve the mechanical strength, in particular, tensile strength, of the silicone rubber, silica filler is often added in the silicone-based hardening composition. However, as a result of conducting diligent research by the present inventors, it was found that the tear strength could be remarkably improved by adding silica filler of which the surface is treated with a specific silica coupling agent in silicone rubber containing a specific matrix containing the linear organopolysiloxane having a vinyl group (A), and the organohydrogen polysiloxane (B) as raw material.

In other words, the present inventors found that the mechanical strength, in particular, tear strength, of silicone rubber could be improved by combining the linear organopolysiloxane having a vinyl group (A), the organohydrogen polysiloxane (B), and the silica filler (C) of which the surface is treated with a silane coupling agent having a trimethylsilyl group in advance (this may be simply denoted by "trimethylsilyl group-surface treated silica filler (C)" below).

Specifically, it was surprisingly found that the tear strength of the silicone rubber could be remarkably improved while maintaining the tensile strength by combining the linear organopolysiloxane having a vinyl group (A), the organohydrogen polysiloxane (B), and the silica filler (C) of which the surface is previously treated with a silane coupling agent having a trimethylsilyl group, compared with a combination between the linear organopolysiloxane having a vinyl group (A), the organohydrogen polysiloxane (B), and the silica filler of which the surface is treated with a silane coupling agent having a methylsilyl group (dimethyl dichlorosilane). In addition, it was also found that the elongation at breaking was remarkably increased while maintaining the tensile strength by combining the linear organopolysiloxane having a vinyl group (A), the organohydrogen polysiloxane (B), and the trimethylsilyl group-surface treated silica filler (C).

As explained above, the reason for improvement of the tear strength of the silicone rubber by using silica filler as filler which is combined between the linear organopolysiloxane having a vinyl group (A), and the organohydrogen polysiloxane (B), and treating the surface of the silica filler with a silane coupling agent having a trimethylsilyl group in advance can be presumed as shown below.

That is, since an increase of the amount of the silica filler in silicone rubber which is obtained by hardening the silicone rubber-based hardening composition containing the linear organopolysiloxane having a vinyl group (A), and the organohydrogen polysiloxane (B), causes the stiffening effects to be increased, the silicone rubber can changed to a hard material having high elasticity. To the contrary of this merit, there is a demerit in that the elongation at breaking of the silicone rubber is decreased by adding a large amount of the silica filler, and thereby, the tear strength is decreased.

In the present invention, it can be presumed that the hydrophobic property of the silica filler is increased by treating the surface of the silica filler with the silane coupling agent having a trimethylsilyl group, and the cohesive force of the silica filler in the silicone rubber-based hardening composition containing the linear organopolysiloxane having a vinyl group (A), the organohydrogen polysiloxane (B) is decreased (condensation due to the hydrogen bond by the silanol group is decreased), and thereby, the dispersibility of the silica filler in the composition is improved. In addition, it can be also presumed that as a result of increase of the hydrophobic property of the silica filler, when the matrix of the silicon rubber, which is obtained by hardening the silicon rubber-based hardening composition, is deformed, the slippage of the silica filler in the matrix is improved. Thereby, it can be presumed that the stiffening effects to the mechanical strength, in particular, tear strength, of the silicone rubber are increased by improvement of the dispersibility and slippage of the silica filler.

In addition, it can be presumed that, in particular, the tear strength among the mechanical strength is improved for the following reasons.

That is, the interface between the silica filler and the rubber matrix is increased by the improvement of the dispersibility of the silica filler, and the number of the rubber molecular chains, which are affected by the silica filler, are increased. Thereby, the stiffening effects due to the silica filler are increased, and the mechanical strength is also improved. The molecular mobility of the rubber molecular chains, which are affected by the silica filler, is decreased by the interaction with the silica filler. Thereby, the rubber molecular chain is hard compared with an area having high molecular mobility. In the tear behavior in silicone rubber, when an initial crack grows and spreads, and tear stress is applied to the hard area, the hard area resists the tear stress. As a result, the tear strength is increased.

Moreover, the silane coupling agent having a dimethylsilyl group has been known as a surface treatment agent for making an inorganic filler hydrophobic. However, as explained above, the silicone rubber obtained by using the silane coupling agent having a dimethylsilyl group has remarkably lower tear strength compared with the silicone rubber obtained by using the silane coupling agent having a trimethylsilyl group. The reason for causing the large difference in the tear strength can be presumed to be because the silane coupling agent having a dimethylsilyl group has lower cohesive-decrease effects compared with the silane coupling agent having a trimethylsilyl group. As a result, it can be presumed that the effects, which are obtained by using the silane coupling agent having a trimethylsilyl group, cannot be obtained by using the silane coupling agent having a dimethylsilyl group. In particular, as explained below, when the amount of the silica filler is increased, the difference in the tear strength is further increased (see Examples and Comparative Examples).

As explained above, the silicone rubber which is obtained by hardening the silicone rubber-based hardening composition according to the present invention has excellent tensile strength and tear strength. Therefore, it is possible to obtain the catheter made of the silicone rubber which is excellent in scratch resistance and kink resistance by using the silicone rubber-based hardening composition according to the present invention.

Below, the components of the silicone rubber-based hardening composition according to the present invention will be explained in detail. The silicone rubber-based hardening composition according to the present invention essentially contains the following components (A) to (C).

(A) Linear Organopolysiloxane Having a Vinyl Group

The linear organopolysiloxane having a vinyl group is a main component in the silicone rubber-based hardening composition according to the present invention, and this is a polymer having a linear structure. This linear organopolysiloxane has a vinyl group, and the vinyl group becomes a crosslinking point when vulcanization is carried out.

The amount of the vinyl group in the linear organopolysiloxane having a vinyl group is not particularly limited. However, the amount of the vinyl group is preferably in a range of 0.01 to 15% by mole, and more preferably in a range of 0.05 to 12% by mole.

Moreover, the amount of the vinyl group in the linear organopolysiloxane having a vinyl group means the molar percentage of the siloxane unit having a vinyl group when the total unit of the linear organopolysiloxane having a vinyl group (A) is assumed to 100% by mole. At this time, one siloxane unit having a vinyl group is regarded to have one vinyl group.

The polymerization degree of the linear organopolysiloxane having a vinyl group (A) is not particularly limited. However, the polymerization degree is generally in a range of 3,000 to 10,000, and preferably in a range of 4,000 to 8,000.

The specific gravity of the linear organopolysiloxane having a vinyl group (A) is generally in a range of 0.9 to 1.1.

The linear organopolysiloxane having a vinyl group (A) preferably has a structure represented by the formula (1) below.

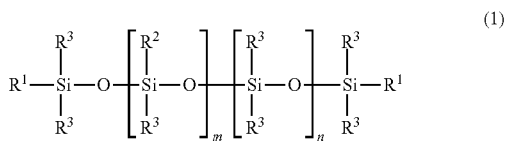

(1)

(in the formula (1), m denotes an integer from 1 to 1,000; n denotes an integer from 3,000 to 10,000; $R^1$ denotes an alkyl group, alkenyl group, aryl group, which contains 1 to 10 carbon atoms, and has a substituted group or no substituted group, or a hydrocarbon group in which these groups are combined; $R^2$ denotes an alkyl group, alkenyl group, aryl group, which contains 1 to 10 carbon atoms, and has a substituted group or no substituted group, or a hydrocarbon group in which these groups are combined; $R^3$ denotes an alkyl group, aryl group, which contains 1 to 8 carbon atoms, and has a substituted group or no substituted group, or a hydrocarbon group in which these groups are combined; and at least one of plural $R^1$ and $R^2$ is an alkenyl group.)

In the formula (1), $R^1$ denotes an alkyl group, alkenyl group, aryl group, which contains 1 to 10 carbon atoms, and has a substituted group or no substituted group, or a hydrocarbon group in which these groups are combined. Examples of the alkyl group which contains 1 to 10 carbon atoms include a methyl group, an ethyl group, and a propyl group. Among these alkyl groups, a methyl group is preferable. Examples of the alkenyl group which contains 1 to 10 carbon atoms include a vinyl group, an allyl group, and a butenyl group. Among these alkenyl groups, a vinyl group is preferable. Examples of the aryl group which contains 1 to 10 carbon atoms include a phenyl group.

$R^2$ denotes an alkyl group, alkenyl group, aryl group, which contains 1 to 10 carbon atoms, and has a substituted group or no substituted group, or a hydrocarbon group in which these groups are combined. Examples of the alkyl group which contains 1 to 10 carbon atoms include a methyl group, an ethyl group, and a propyl group. Among these alkyl groups, a methyl group is preferable. Examples of the alkenyl group which contains 1 to 10 carbon atoms include a vinyl group, an allyl group, and a butenyl group. Examples of the aryl group which contains 1 to 10 carbon atoms include a phenyl group.

$R^3$ denotes an alkyl group, aryl group, which contains 1 to 8 carbon atoms, and has a substituted group or no substituted group, or a hydrocarbon group in which these groups are combined. Examples of the alkyl group which contains 1 to 8 carbon atoms include a methyl group, an ethyl group, and a propyl group. Among these alkyl groups, a methyl group is preferable. Examples of the aryl group which contains 1 to 8 carbon atoms include a phenyl group.

Examples of the substituted group in $R^1$ and $R^2$ which have a substituted group in the formula (1) include a methyl group, and a vinyl group. Examples of the substituted group in $R^3$ which has a substituted group in the formula (1) include a methyl group.

Moreover, in the formula (1), plural $R^1$ are independent to each other, and may be the same or not. Plural $R^2$ and $R^3$ are independent to each other, and may be the same or not, similar to $R^1$.

However, at least one of plural $R^1$ and $R^2$ has a vinyl group. That is, at least one of plural $R^1$ and $R^2$ is an alkenyl group.

In the formula (1), m and n are the number of repeating units that constitute the linear organopolysiloxane having a vinyl group (A) represented by the formula (1), m is an integer from 1 to 1,000, and n is an integer from 3,000 to 10,000. m is preferably in a range of 40 to 700, and n is preferably in a range of 3,600 to 8,000.

A specific structure of the linear organopolysiloxane having a vinyl group (A) represented by the formula (1) includes the following structure represented by the formula (1-1) below.

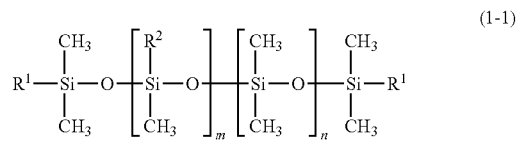

(1-1)

In the formula (1-1), $R^1$ and $R^2$ are independently a methyl group or a vinyl group, and at least one of $R^1$ and $R^2$ is a vinyl group.

In the present invention, it is preferable that the linear organopolysiloxane having a vinyl group (A) contain a first linear organopolysiloxane having a vinyl group (A1) containing 0.2% by mole or less of a vinyl group, and a second linear organopolysiloxane having a vinyl group (A2) containing 0.5% by mole to 12% by mole of a vinyl group. The first linear organopolysiloxane having a vinyl group (A1) may contain 0.01% by mole to 0.2% by mole, preferably 0.01% by mole to 0.15% by mole, of a vinyl group. It is possible to locally present the vinyl group by combining the first linear organopolysiloxane having a vinyl group (A1) which has a general vinyl group content and the second linear organopolysiloxane having a vinyl group (A2) which has a high vinyl group content as the crude rubber which is the raw material of the silicone rubber. Thereby, it is possible to effectively form sparse and dense crosslinking density in the crosslinking network of the silicone rubber. That is, it is possible to effectively improve the tear strength of the silicone rubber.

Specifically, it is preferable to use the first linear organopolysiloxane having a vinyl group (A1) containing 0.01% by mol to 0.15% by mole of a unit including a vinyl group as R' and/or a unit including a vinyl group as $R^2$ in the formula (1-1), and the second linear organopolysiloxane having a vinyl group (A2) containing 0.50% by mole to 12% by mole of a unit including a vinyl group as $R^1$ and/or a unit including a vinyl group as $R^2$ in the formula (1-1) as the linear organopolysiloxane having a vinyl group (A).

It is preferable that the first linear organopolysiloxane having a vinyl group (A1) contain 0.1 to 0.15% by mole of a vinyl group, and the second linear organopolysiloxane having a vinyl group (A2) contain 0.8 to 8.0% by mole of a vinyl group.

When the first linear organopolysiloxane having a vinyl group (A1) and the second linear organopolysiloxane having a vinyl group (A2) are used in combination, the ratio between the first linear organopolysiloxane having a vinyl group (A1) and the second linear organopolysiloxane having a vinyl group (A2) is not particularly limited. However, the weight ratio ((A1):(A2)) between them is preferably in a range of 1:0.05 to 1:0.6, in particular, 1:0.08 to 1:0.5 is more preferable.

It is possible to use only one kind of the first linear organopolysiloxane having a vinyl group (A1) and the second linear organopolysiloxane having a vinyl group (A2) respectively. In addition, two or more kinds of them can also be used.

(B) Organohydrogen Polysiloxane

The organohydrogen polysiloxane (B) has a linear structure and a structure (≡Si—H) in which Si is directly connected with hydrogen. The organohydrogen polysiloxane (B) causes a hydrosilylation reaction with a vinyl group in a component added in the silicone rubber-based hardening composition to make a crosslink, in addition to the vinyl group in the linear organopolysiloxane having a vinyl group (A).

In the organohydrogen polysiloxane (B), the amount of the hydrogen atom which is directly bonded with Si, that is, the amount of a hydride group, is not particularly limited. In the silicone rubber-based hardening composition, the amount of the hydride group in the organohydrogen polysiloxane (B) is preferably in a range of 0.5 to 5 moles, and more preferably in a range of 1 to 3.5 moles relative to 1 mole of the vinyl group in the linear organopolysiloxane having a vinyl group (A).

The molecular weight of the organohydrogen polysiloxane (B) is not particularly limited. However, the weight average molecular weight of the organohydrogen polysiloxane (B) is preferably 20,000 or less, and in particular, 7,000 is more preferable. The weight average molecular weight of the organohydrogen polysiloxane (B) can be measured by using GPC (Gel Permeation Chromatography).

In general, it is preferable that the organohydrogen polysiloxane (B) do not contain a vinyl group, because there is a possibility that the crosslinking reaction may be promoted in the molecule thereof.

It is preferable that the organohydrogen polysiloxane (B) have a structure represented by the following formula (2).

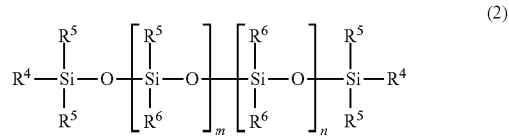

(in the formula (2), m denotes an integer from 2 to 500; n denotes an integer from 2 to 400; m and n satisfy 20≤(m+n)≤500; $R^4$ denotes an alkyl group, alkenyl group, aryl group, which contains 1 to 10 carbon atoms, and has a substituted group or no substituted group, a hydrocarbon group in which these groups are combined, or a hydride group; $R^5$ denotes an alkyl group, alkenyl group, aryl group, which contains 1 to 10 carbon atoms, and has a substituted group or no substituted group, a hydrocarbon group in which these groups are combined, or a hydride group; at least two of plural $R^4$ and $R^5$ are a hydride group; and $R^6$ denotes an alkyl group, aryl group, which contains 1 to 8 carbon atoms, and has a substituted group or no substituted group, or a hydrocarbon group in which these groups are combined.) In a preferred embodiment, m denotes an integer from 0 to 300; and n denotes an integer represented by (300−m).

In the formula (2), $R^4$ denotes an alkyl group, alkenyl group, aryl group, which contains 1 to 10 carbon atoms, and has a substituted group or no substituted group, a hydrocarbon group in which these groups are combined, or a hydride group. Examples of the alkyl group which contains 1 to 10 carbon atoms include a methyl group, an ethyl group, and a propyl group. Among these alkyl groups, a methyl group is preferable. Examples of the alkenyl group which contains 1 to 10 carbon atoms include a vinyl group, an allyl group, and a butenyl group. Among these alkenyl groups, a vinyl group is preferable. Examples of the aryl group which contains 1 to 10 carbon atoms include a phenyl group.

In the formula (2), $R^5$ denotes an alkyl group, alkenyl group, aryl group, which contains 1 to 10 carbon atoms, and has a substituted group or no substituted group, a hydrocarbon group in which these groups are combined, or a hydride group. Examples of the alkyl group which contains 1 to 10 carbon atoms include a methyl group, an ethyl group, and a propyl group. Among these alkyl groups, a methyl group is preferable. Examples of the alkenyl group which contains 1 to 10 carbon atoms include a vinyl group, an allyl group, and a butenyl group. Among these alkenyl groups, a vinyl group is preferable. Examples of the aryl group which contains 1 to 10 carbon atoms include a phenyl group.

Moreover, in the formula (2), plural $R^4$ are independent to each other, and may be the same or not. Plural $R^5$ are independent to each other, and may be the same or not, similar to $R^4$.

However, at least two of plural $R^4$ and $R^5$ are a hydride group.

In the formula (2), $R^6$ is an alkyl group, aryl group, which contains 1 to 8 carbon atoms, and has a substituted group or no substituted group, or a hydrocarbon group in which these groups are combined. Examples of the alkyl group which contains 1 to 8 carbon atoms include a methyl group, an ethyl group, and a propyl group. Among these alkyl groups, a methyl group is preferable. Examples of the aryl group which contains 1 to 8 carbon atoms include a phenyl group. Plural $R^6$ are independently, and may be the same or not.

Examples of the substituted group in $R^4$, $R^5$, and $R^6$ which have a substituted group in the formula (2) include a methyl group, and a vinyl group. Among these, a methyl group is preferable because a methyl group can prevent the cross-linking reaction in the molecule.

m and n are the number of repeating units that constitute the organohydrogen polysiloxane (B) represented by the formula (2), m is an integer from 2 to 500, n is an integer from 2 to 400, and m and n satisfy 20≤(m+n)≤500. m is preferably in a range of 2 to 300, n is preferably from 2 to 200, and m and n preferably satisfy 40≤(m+n)≤300. When m and n satisfy 20≤(m+n)≤500, preferably 40≤(m+n)≤300, crosslinking reaction can be appropriately carried out, and tear resistance of the silicone rubber can be improved. In a preferred embodiment, m is an integer of 0 to 300, and n is an integer of (300−m). In a particularly preferred embodiment, m is in a range of 0 to 150, and n is preferably an integer of (150−m).

The organohydrogen polysiloxane (B) may be used alone or in combination of two or more.

(C) Trimethylsilyl Group-Surface Treated Silica Filler (C)

The trimethylsilyl group-surface treated silica filler (C) is silica filler of which the surface is treated with a silane coupling agent having a trimethylsilyl group [$(CH_3)_3$—Si—] (this may be simply denoted by "trimethylsilyl group containing coupling agent") in advance.

In the present invention, the surface treatment of the silica filler with the silane coupling agent having a trimethylsilyl group means a treatment in which the hydroxyl group bonded with a silicon atom (silanol group: Si—OH) on the surface of the silica filler is replaced with a functional group containing a trimethylsilyl group derived from the silane coupling agent having a trimethylsilyl group, or a treatment in which a functional group containing a trimethylsilyl group derived from the silane coupling agent having a trimethylsilyl group is applied on the surface of the silica filler.

The silane coupling agent having a trimethylsilyl group has a functional group containing a trimethylsilyl group and a hydrolyzable group. Under conditions in which hydrolysis can be carried out, the hydrolyzable group is hydrolyzed and a hydroxyl group is generated. The functional group containing a trimethylsilyl group means a trimethylsilyl group itself or a group containing a trimethylsilyl group as a part thereof.

In the present invention, the silane coupling agent having a trimethylsilyl group typically has a structure in which a silicon atom in the trimethylsilyl group is bonded with the hydrolyzable group. Under conditions in which hydrolysis can be carried out, the hydrolyzable group is hydrolyzed and a silanol, in which the silicon atom in the trimethylsilyl group is bonded with the hydroxyl group, is generated.

The hydroxyl group (typically silanol), which is generated by the hydrolysis of the hydrolyzable group in the silane coupling agent having a trimethylsilyl group, makes a dehydration condensation reaction with the hydroxyl group on the surface of the silica filler. Thereby, the functional group containing a trimethylsilyl group of the silane coupling agent is covalently bonded with the silicon atom of the silica filler via an oxygen atom (O). Typically, the silicon atom of the trimethylsilyl group in the silane coupling agent and the silicon atom in the silica filler make a covalent bond via an oxygen atom (O).

As explained above, the hydroxyl group of the silanol group on the surface of the silica filler is replaced with the functional group containing a trimethylsilyl group.

Examples of the silica filler of which the surface is treated with the silane coupling agent having a trimethylsilyl group include dried silica and wet silica. In particular, dried silica is preferable from the viewpoint of extrusion moldability of the silicone rubber, and fumed silica is more preferable.

Any silane coupling agent having a trimethylsilyl group can be used as long as it has a trimethylsilyl group and generates a hydroxyl group under conditions in which hydrolysis can be carried out, and has a hydrolyzable group which can cause a dehydration condensation reaction with the hydroxyl group in the silanol group on the surface of the silica filler. Examples of the silane coupling agent having a trimethylsilyl group include silazane, chlorosilane and alkoxysilane.

Any silazane can be used as long as it has a structure in which the silicon atom in the trimethylsilyl group is bonded with a nitrogen atom. Examples of the silazane used include hexamethyldisilazane.

Any chlorosilane can be used as long as it has a structure in which the silicon atom in the trimethylsilyl group is bonded with a chlorine atom. Examples of the chlorosilane used include trimethylchlorosilane.

Any alkoxysilane can be used as long as it has a structure in which the silicon atom in the trimethylsilyl group is bonded with an alkoxy group. Examples of the alkoxysilane used include trimethylmethoxysilane, and trimethylethoxysilane.

Among these, at least one selected from the group consisting of hexadimethyldisilazane, trimethylchlorosilane, trimethylmethoxysilane, and trimethylethoxysilane is preferably used.

The degree of the surface treatment of the silica filler with the silane coupling agent having a trimethylsilyl group is not particularly limited because a preferable degree varies depending on the kind of the silane coupling agent used, the surface area of the silica filler, and the like. However, the surface treatment is preferably carried out at a certain degree so that the trimethylsilyl group-surface treated silica filler (C) after the surface treatment contains 0.1 to 7.0% by weight, preferably 1.0 to 4.0% by weight, and more preferably 1.5 to 3.0% by weight of carbon atom. The carbon content in the trimethylsilyl group-surface treated silica filler (C) is relevant to the carbon content in organic groups derived from the silane coupling agent which is chemically bonded with the surface of the silica filler. The carbon content gives an indication of the surface treatment degree of the silica filler by the silane coupling agent.

It is possible to remarkably improve the tear strength and tensile strength, in particular, tear strength of the silicone rubber by adjusting the carbon content of the trimethylsilyl group-surface treated silica filler (C) in the above mentioned range.

The carbon content of the trimethylsilyl group-surface treated silica filler (C) can be calculated in the following manner.

That is, the carbon content can be calculated by thermally decomposing the trimethylsilyl group-surface treated silica filler (C) under oxygen atmosphere at 1,000 to 1,200° C. using a trace carbon analyzer, and measuring the amount of $CO_2$ generated.

It is preferable that all of the hydroxyl groups in the silanol group on the surface of the trimethylsilyl group-surface treated silica filler (C) be replaced with a functional group containing the trimethylsilyl group derived from the silane coupling agent having a trimethylsilyl group.

Any surface treatment methods using the silane coupling agent having a trimethylsilyl group can be used without limitations. For example, a method disclosed in Published Japanese Translation No. 2007-526373 of the PCT International Publication can be used.

Specifically, a method in which after spraying water to the silica filler (non-treated silica filler), of which the surface is not treated with the silane coupling agent having a trimethylsilyl group, the silane coupling agent having a trimethylsilyl group is also sprayed to the silica filler, and then the silica filler is thermally treated, can be used. The water used may be acidified (for example, pH 1 to 7) using an acid such as hydrochloric acid. The silane coupling agent used may be dissolved in an appropriate solvent if necessary.

The spraying of water or the silane coupling agent can be carried out using a one-fluid nozzle, two-fluid nozzle, or ultrasonic nozzle. It is preferable that the spraying be carried out in a vessel provided with a mixing means while stirring the silica filler. After spraying of water and the silane coupling agent, if necessary, the silica filler and water and/or the silica coupling agent may be mixed. The temperature and the time in the thermal treatment can be adjusted, and for example, the thermal treatment may be carried out at 20 to 400° C. for 0.1 to 6 hours. The thermal treatment can also be carried out under inert gas atmosphere such as nitrogen gas.

Otherwise, a method, in which the non-treated silica filler is subjected to the vapor of the silane coupling agent, and then heated (for example, 50 to 800° C.), can also be used. The thermal treatment can also be carried out under inert atmosphere.

It is preferable that the trimethylsilyl group-surface treated silica filler (C) have a specific surface area of 30 $m^2/g$ or more, more preferably 100 $m^2/g$ or more, and 500 $m^2/g$ or less, and more preferably 300 $m^2/g$ or less. The specific surface area is most preferably in a range of 30 to 500 $m^2/g$.

The specific surface area of the trimethylsilyl group-surface treated silica filler (C) can be measured by a common method, for example, BET specific surface area method can be used.

In addition, it is preferable that the average primary particle diameter of the trimethylsilyl group-surface treated silica filler (C) be 100 nm or less, and in particular, 20 nm or less is preferable.

The average primary particle diameter of the trimethylsilyl group-surface treated silica filler (C) can be measured by a common method.

The trimethylsilyl group-surface treated silica filler (C) can be used alone or in combination of two or more. For example, the silica fillers (C), of which the surface is treated with different silane coupling agent having a trimethylsilyl groups, may be combined.

The silicone rubber-based hardening composition according to the present invention may contain components in addition to the components (A) to (C). As the component which may be added in addition to the components (A) to (C), platinum or a platinum compound (E), which is explained below, can be used.

(E) Platinum or Platinum Compound

Platinum or a platinum compound (E) acts a catalyst for vulcanization. The amount used is a catalyst amount. As the platinum or a platinum compound (E), well-known components can be used. Examples of the platinum or the platinum compound (E) used include platinum black, a support in which platinum is supported on silica or carbon black, chloroplatinic acid, an alcohol solution of chloroplatinic acid, a complex of chloroplatinic acid and olefin, and a complex of chloroplatinic acid and vinylsiloxane. The platinum or a platinum compound (E), which is a catalyst component, may be used alone or in combination of two or more.

The silicone rubber-based hardening composition according to the present invention may contain a well-known component which is added in the silicone rubber-based hardening composition in addition to the components (A) to (C), and (E). Examples of the component include diatom earth, iron oxide, zinc oxide, titanium oxide, barium oxide, magnesium oxide, cerium oxide, calcium carbonate, magnesium carbonate, zinc carbonate, glass-wool, and mica. In addition, a dispersant, pigment, die, antistatic agent, antioxidant, flame retardant, heat conduction improver. An appropriate amount of these components can be added in the silicone rubber-based hardening composition according to the present invention.

In the silicone rubber-based hardening composition according to the present invention, the content of each component is not particularly limited. However, in general, it is preferable that the silicone rubber-based hardening composition contain 0.1 to 10 parts by weight of the organohydrogen polysiloxane (B), and 15 to 150 parts by weight of the trimethylsilyl group-surface treated silica filler (C), relative to 100 parts by weight of the linear organopolysiloxane having a vinyl group (A). More preferably, the silicone rubber-based hardening composition contain 0.5 to 8 parts by weight of the organohydrogen polysiloxane (B), and 15 to 100 parts by weight of the trimethylsilyl group-surface treated silica filler (C), relative to 100 parts by weight of the linear organopolysiloxane having a vinyl group (A). It is also preferable that the silicone rubber-based hardening composition contain 0.5 to 4 parts by weight of the organohydrogen polysiloxane (B), and 18.3 to 70 parts by weight of the trimethylsilyl group-surface treated silica filler (C), relative to 100 parts by weight of the linear organopolysiloxane having a vinyl group (A).

The amount of platinum or the platinum compound (E) used is a catalyst amount, and can be appropriately adjusted. However, the content of platinum or the platinum compound (E) is preferably in a range of 0.05 to 5 parts by weight, and more preferably in a range of 0.1 to 1 part by weight relative to 100 parts by weight of the linear organopolysiloxane having a vinyl group (A).

The silicone rubber-based hardening composition according to the present invention can be obtained by uniformly mixing the components explained above using a kneading device. Examples of the kneading device include kneader, two-roller, Banbury mixer (continuous kneader), and pressurized kneader.

Platinum or the platinum compound (E) which is a catalyst is preferably dispersed in the linear organopolysiloxane having a vinyl group (A) from the viewpoint of ease of handling.

The silicone rubber can be obtained by heating the silicone rubber-based hardening composition according to the present invention which is obtained as explained above at 140 to 180° C. for 5 to 15 minutes (first hardening), and then post-baking at 200° C. for 4 hours (second hardening).

The silicone rubber, which is excellent in the tear strength and tensile strength, in particular, tear strength, can be obtained by hardening the silicone rubber-based hardening composition according to the present invention.

In addition, the silicone rubber, which has 1,000% or more of an elongation at breaking (strain) of a dumb-bell shaped third test piece according to JIS K 6251 (2004), can be obtained by hardening the silicone rubber-based hardening composition according to the present invention.

In other words, according to the present invention, the silicone rubber having high elongation even when the silicone rubber contains a large amount of the silica filler can be obtained.

In addition, the silicone rubber, which can extend at 100 mm or more before breaking a crescent-shaped test piece according to JIS K 6252 (2001), can be obtained.

In other words, according to the present invention, the silicone rubber having high elongation even when the silicone rubber contains a large amount of the silica filler can be obtained.

In the present invention, the tensile strength and elongation at breaking are based on JIS K 6251 (2004) except that the thickness of the test piece which is obtained by hardening the silicone rubber-based hardening composition is adjusted to 1 mm.

In addition, the tear strength and stroke are based on JIS K 6252 (2001) except that the thickness of the test piece which is obtained by hardening the silicone rubber-based hardening composition is adjusted to 1 mm.

The molded articles having excellent mechanical strength explained above can be obtained by using the silicone rubber having such tensile strength and tear strength. In addition, the medical tube (for example, catheter) made of silicone rubber which is excellent in kink resistance and scratch resistance by using the molded article.

In another silicone rubber-based hardening composition according to the present invention, the silicone rubber-based hardening composition preferably further contains silica filler (D), of which the surface is treated with a silane coupling agent having an organosilyl group containing a vinyl group.

In order to improve the mechanical strength of the silicone rubber, silica filler is often added in the silicone based hardening composition. However, as a result of conducting diligent research by the present inventors, it was found that the balance between the tensile strength, tear strength, and hardness could be remarkably improved by adding two kinds of silica filler in combination of which the surface is treated with a specific silica coupling agent in silicone rubber containing a specific matrix containing the linear organopolysiloxane having a vinyl group (A), and the organohydrogen polysiloxane (B) as raw material.

In other words, the present inventors found that the mechanical strength, in particular, the balance between the tensile strength, tear strength, and hardness of silicone rubber could be improved by combining the linear organopolysiloxane having a vinyl group (A) and the organohydrogen polysiloxane (B); and the silica filler (C) (this may be simply denoted by "silicon filler (C)" below) of which the surface is treated with a silane coupling agent having a trimethylsilyl group in advance, and silica filler (D) of which the surface is treated with a silane coupling agent having an organosilyl group containing a vinyl group (this may be simply denoted by "silicon filler (D)" below).

As explained above, the reason for improvement of the balance between the tensile strength, tear strength, and hardness of the silicone rubber in this embodiment can be presumed as shown below.

That is, an increase of the amount of the silica filler in silicone rubber which is obtained by hardening the silicone rubber-based hardening composition containing the linear organopolysiloxane having a vinyl group (A), and the organohydrogen polysiloxane (B), causes the stiffening effects to be increased, and the silicone rubber can changed to a hard material having high elasticity. To the contrary of this merit, there is a demerit in that the elongation at breaking of the silicone rubber is decreased by adding a large amount of the silica filler, and thereby, the tear strength is decreased.

In this embodiment, these demerits due to the silica filler can be solved and properties of the silicone rubber can be improved by using both of the silica filler (C) of which the surface is treated with a silane coupling agent having a trimethylsilyl group in advance, and the silica filler (D) of which the surface is treated with a silane coupling agent having an organosilyl group containing a vinyl group.

The silica filler (C) has high hydrophobic properties because the surface of the silica filler (C) is previously treated with the silane coupling agent having a trimethylsilyl group. As a result, it can be presumed that the cohesive force of the silica filler (C) is decreased (condensation due to the hydrogen bond by the silanol group is decreased) in the silicone rubber-based hardening composition containing the linear organopolysiloxane having a vinyl group (A), and the organohydrogen polysiloxane (B) is decreased, and thereby, the dispersibility of the silica filler (C) in the composition is improved. In addition, it can be also presumed that as a result of increase of the hydrophobic property of the silica filler (C), when the matrix of the silicon rubber, which is obtained by hardening the silicon rubber-based hardening composition, is deformed, the slippage of the silica filler (C) in the matrix is improved. Thereby, it can be presumed that the stiffening effects to the mechanical strength (for example, tensile strength, tear strength, and the like), in particular, tear strength of the silicone rubber are increased by improvement of the dispersibility and slippage of the silica filler.

In addition, it can be presumed that, in particular, the tear strength among the mechanical strength is improved for the following reasons.

That is, the interface between the silica filler (C) and the rubber matrix is increased by improving the dispersibility of the silica filler (C), and the rubber molecular chains, which are affected by the silica filler, are increased. Thereby, the stiffening effects due to the silica filler are increased, and the mechanical strength is also improved. The molecular mobility of the rubber molecular chains, which are affected by the silica filler, is decreased by the interaction with the silica filler. Thereby, the rubber molecular chain is hard compared with an area having high molecular mobility. In the tear behavior in silicone rubber, when an initial crack grows and spreads, and tear stress is applied to the hard area, the hard area resists the tear stress. As a result, the tear strength is increased.

The silica filler (D) is previously subjected to a surface treatment using a silane coupling agent having an organosilyl group containing a vinyl group. Therefore, the surface of the silica filler (D) has a vinyl group. The vinyl group becomes a crosslinking point when vulcanization is carried out. In other words, a covalent bond is generated between the silica filler (D) and a matrix containing the linear organopolysiloxane having a vinyl group (A) and the organohydrogen polysiloxane (B) in the silicone rubber obtained by hardening the silicone rubber-based hardening composition according to this embodiment. Because of the reason as presumed above, the hardness can be improved while maintaining high tear strength of the silicone rubber by forming a rubber matrix-silica filler network in the silicone rubber.

As explained above, the silicone rubber which is obtained by hardening the silicone rubber-based hardening composition in this embodiment has excellent tear strength and hardness. Therefore, it is possible to obtain the catheter made of the silicone rubber which is excellent in kink resistance, scratch resistance, and ease of insertion by using the silicone rubber-based hardening composition according to this embodiment.

(D) Silica Filler of which the Surface is Treated with a Silane Coupling Agent Having an Organosilyl Group Containing a Vinyl Group The surface of the silica filler (D) is treated with a silane coupling agent having an organosilyl group containing a vinyl group in advance.

In the present invention, the surface treatment of the silica filler with the silane coupling agent having an organosilyl group containing a vinyl group means a treatment in which the hydroxyl group bonded with a silicon atom (silanol group: Si—OH) on the surface of the silica filler is replaced with a functional group containing an organosilyl group containing a vinyl group derived from the silane coupling agent having an organosilyl group containing a vinyl group, or a treatment in which an organosilyl group containing a vinyl group derived from the silane coupling agent having an organosilyl group containing a vinyl group is applied on the surface of the silica filler.

The silane coupling agent having an organosilyl group containing a vinyl group has a functional group containing an organosilyl group containing a vinyl group and a hydrolyzable group. Under conditions in which hydrolysis can be carried out, the hydrolyzable group is hydrolyzed and a hydroxyl group is generated.

The organosilyl group containing a vinyl group means a group ($CH_2$=CH—Si≡) in which at least one vinyl group is directly bonded with a silicon atom or a group ($CH_2$=CH—W—Si≡) in which at least one vinyl group is bonded with a silicon atom via a linking group W. Examples of the linking group W include an alkyl group, ether group, and ester group.

The functional group containing an organosilyl group containing a vinyl group means an organosilyl group containing a vinyl group itself or a group containing an organosilyl group containing a vinyl group as a part thereof.

In this embodiment, the silane coupling agent having an organosilyl group containing a vinyl group typically has a structure in which a silicon atom in the organosilyl group containing a vinyl group is bonded with at least one hydrolyzable group. Under conditions in which hydrolysis can be carried out, the hydrolyzable group is hydrolyzed and a silanol, in which the silicon atom in the organosilyl group containing a vinyl group is bonded with the at least one hydroxyl group, is generated.

The hydroxyl group (typically silanol), which is generated by the hydrolysis of the hydrolyzable group in the silane coupling agent having an organosilyl group containing a vinyl group, makes a dehydration condensation reaction with the hydroxyl group on the surface of the silica filler. Thereby, the functional group containing the organosilyl group containing a vinyl group of the silane coupling agent is covalently bonded with the silicon atom of the silica filler via an oxygen atom (O). Typically, the silicon atom of the organosilyl group containing a vinyl group in the silane coupling agent and the silicon atom in the silica filler make a covalent bond via an oxygen atom (O).

As explained above, the hydroxyl group of the silanol group on the surface of the silica filler is replaced with the functional group containing the organosilyl group containing a vinyl group.

Examples of the silica filler of which the surface is treated with the silane coupling agent having an organosilyl group containing a vinyl group include dried silica and wet silica. In particular, dried silica is preferable from the viewpoint of extrusion moldability of the silicone rubber, and fumed silica is more preferable.

Any silane coupling agent having an organosilyl group containing a vinyl group can be used as long as it has an organosilyl group containing a vinyl group and generates a hydroxyl group under conditions in which hydrolysis can be carried out, and has a hydrolyzable group which can cause a dehydration condensation reaction with the hydroxyl group in the silanol group on the surface of the silica filler. Examples of the silane coupling agent having an organosilyl group containing a vinyl group include silazane, chlorosilane and alkoxysilane.

Any silazane can be used as long as it has a structure in which the silicon atom in the organosilyl group containing a vinyl group is bonded with at least one nitrogen atom. Examples of the silazane used include divinyl tetramethyldisilazane.

Any chlorosilane can be used as long as it has a structure in which the silicon atom in the organosilyl group containing a vinyl group is bonded with at least one chlorine atom. Examples of the chlorosilane used include vinyltrichlorosilane.

Any alkoxysilane can be used as long as it has a structure in which the silicon atom in the organosilyl group containing a vinyl group is bonded with at least one alkoxy group. Examples of the alkoxysilane used include methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane.

It is preferable that all of the hydroxyl group in the silanol group on the surface of the silica filler (D) be replaced with the functional group containing an organosilyl group containing a vinyl group derived from the silane coupling agent having an organosilyl group containing a vinyl group.

Any surface treatment methods using the silane coupling agent having an organosilyl group containing a vinyl group can be used without limitations.

Specifically, a method in which silica filler is put in a mixer, first, water and then the silane coupling agent having an organosilyl group containing a vinyl group, such as methacryloxypropyltriethoxysilane are added in the silica filler while stirring, they are mixed at 30° C. for 15 minutes, dried in an oven at 100° C. for about 1 hour, and then cooled.

It is preferable that the silica filler (D) have a specific surface area of 30 $m^2$/g or more, more preferably 100 $m^2$/g or more, and 500 $m^2$/g or less, and more preferably 300 $m^2$/g or less. The specific surface area is most preferably in a range of 30 to 500 $m^2$/g. The specific surface area of the silica filler (D) can be measured by a common method, for example, BET specific surface area method can be used.

In addition, it is preferable that the average primary particle diameter of the silica filler (D) be 100 nm or less, and in particular, 20 nm or less is preferable. The average primary particle diameter of the silica filler (D) can be measured by a common method.

The silica filler (D) can be used alone or in combination of two or more. For example, the silica fillers (D), of which the surface is treated with a different silane coupling agent having an organosilyl group containing a vinyl group, may be combined.

In the silicone rubber-based hardening composition in this embodiment, the content of each component is not particularly limited. However, in general, it is preferable that the silicone rubber-based hardening composition contain 0.1 to 10 parts by weight of the organohydrogen polysiloxane (B), 15 to 150 parts by weight of the silica filler (C), and 0 to 40 parts by weight of the silica filler (D), relative to 100 parts by weight of the linear organopolysiloxane having a vinyl group (A). In particular, it is preferable that the silicone rubber-based hardening composition contain 0.5 to 8 parts by weight of the organohydrogen polysiloxane (B), 15 to 100 parts by weight of the silica filler (C), and 0 to 35 parts by weight of the silica filler (D), relative to 100 parts by weight of the linear organopolysiloxane having a vinyl group (A). It is more preferable that the silicone rubber-based hardening composition contain 0.5 to 7.65 parts by weight of the organohydrogen polysiloxane (B), 18.3 to 70 parts by weight of the silica filler (C), and 0 to 33.3 parts by weight of the silica filler (D), relative to 100 parts by weight of the linear organopolysiloxane having a vinyl group (A).

It is possible to obtain silicone rubber having a type A-durometer hardness according to JIS K 6253 (2006) of 55 or more by hardening the silicone rubber-based hardening composition according to this embodiment.

The type A-durometer hardness is preferably 55 or more, and in particular 58 or more is preferable.

A molded article having excellent mechanical strength can be obtained by using the silicone rubber having such hardness. In addition, the medical tube (for example, catheter) made of silicone rubber, which is excellent in mechanical strength, such as ease of insertion, can also be obtained by using the molded article.

In addition, the silicone rubber, which has long elongation (strain) at break of a dumb-bell shaped third test piece according to JIS K 6251 (2004) or long elongation (stroke) before breaking a crescent-shaped test piece according to JIS K 6252 (2001), can be obtained by hardening the silicone rubber-based hardening composition according to this embodiment.

In the present invention, the tear strength and stroke are based on JIS K 6252 (2001) except that the thickness of the test piece which is obtained by hardening the silicone rubber-based hardening composition is adjusted to 1 mm.

In addition, the type A durometer hardness is based on JIS K 6253 (2006), and can be measured using the test piece which is obtained by hardening the silicone rubber-based hardening composition.

In addition, the tensile strength and elongation at breaking are based on JIS K 6251 (2004) except that the thickness of the test piece which is obtained by hardening the silicone rubber-based hardening composition in this embodiment is adjusted to 1 mm.

EXAMPLES

Below, embodiments of the silicone rubber-based hardening composition according to the present invention will be explained referring to Examples. However, the present invention is not limited by Examples.

The following materials were used in Examples 1 to 5, Comparative Examples 1 to 4, and Additional Examples 1 to 4.

(A1): first linear organopolysiloxane containing a vinyl group, the content of a vinyl group: 0.13% by mole, and this was synthesized by the following synthesis scheme.

(A2): second linear organopolysiloxane containing a vinyl group, the content of a vinyl group: 0.92% by mole, and this was synthesized by the following synthesis scheme.

(B): organohydrogen polysiloxane made by Momentive Inc. trade name: TC-25D (C1): silica filler of which the surface is treated with hexamethyldisilazane made of Nippon Aerosil Co., Ltd., trade name: Aerosil® RX200, specific surface area: 200 m$^2$/g; average primary particle diameter: 12 nm; and carbon content: 2.5% by weight (C2): silica filler of which the surface is treated with hexamethyldisilazane made of Nippon Aerosil Co., Ltd., trade name: Aerosil® RX300, specific surface area: 300 m$^2$/g; average primary particle diameter: 7 nm; and carbon content: 3.5% by weight (c1): silica filler of which the surface is not treated made of Nippon Aerosil Co., Ltd., trade name: Aerosil® 200, specific surface area: 200 m$^2$/g; and average primary particle diameter: 12 nm (c2): silica filler of which the surface is treated with dimethyldichlorosilane made of Nippon Aerosil Co., Ltd., trade name: Aerosil® R972, specific surface area: 130 m$^2$/g; and average primary particle diameter: 16 nm (c3): silica filler of which the surface is treated with dimethyldichlorosilane made of Nippon Aerosil Co., Ltd., trade name: Aerosil® R974, specific surface area: 200 m$^2$/g; and average primary particle diameter: 12 nm (E) Platinum made by Momentive Inc. trade name: TC-25A

[Synthesis of First Linear Organopolysiloxane Containing a Vinyl Group (A1)]

Based on the following formula (3), the first linear organopolysiloxane containing a vinyl group (A1) was synthesized.

Specifically, 74.7 g (252 mmol) of octamethylcyclotetrasiloxana, 0.086 g (0.25 mmol) of 2,4,6,8-tetramethyl 2,4,6,8-tetravinylcyclotetrasiloxane, and 0.1 g of potassium siliconate were put into a 300 mL-separable flask provided with a cooling pipe, and an impeller, of which the inside was replaced with Ar gas. Then, the temperature was raised, and the mixture was stirred at 120° C. for 30 minutes. After that, raising of the viscosity of the mixture was confirmed.

Then, the temperature was further increased to 155° C., and stirred for 3 hours. After 3 hours, 0.1 g (0.6 mmol) of 1,3-divinyltetramethyldisiloxane was added, and the mixture was stirred at 155° C. for 4 hours.

After 4 hours, the product was diluted with 250 mL of toluene, and washed with water 3 times. After washing, the organic phase was reprecipitated by washing with 1.5 L of methanol several times and purified to separate an oligomer and a polymer. The obtained polymer was dried at 60° C. under reduced pressure overnight, and the first linear organopolysiloxane containing a vinyl group (A1) (Mn: 277, 734; Mw: 573, 906; IV value (dl/g): 0.89) was produced.

Formula (3)

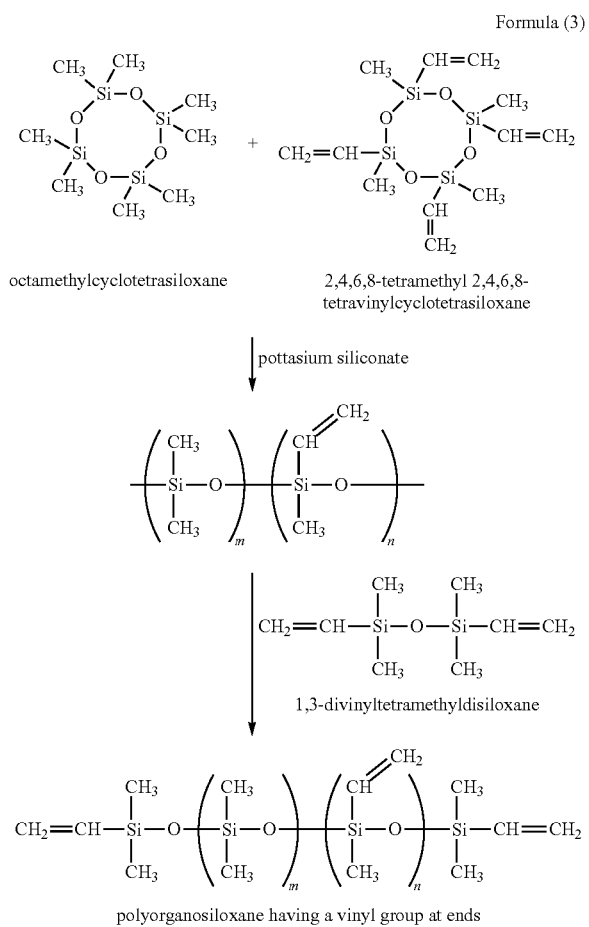

[Synthesis of Second Linear Organopolysiloxane Containing a Vinyl Group (A2)]

The second linear organopolysiloxane containing a vinyl group (A2) was synthesized in a manner identical to that of the first linear organopolysiloxane containing a vinyl group (A1) except that 0.86 g (2.5 mmol) of 2,4,6,8-tetramethyl 2,4,6,8-tetravinylcyclotetrasiloxane was used.

Example 1

Preparation of Silicone Rubber-Based Hardening Composition 50 parts by weight of the silica filler (C1) was added in 100 parts by weight of the first linear organopolysiloxane having a vinyl group (A1), and kneaded to prepare a master batch.

Then, 0.5 parts by weight of platinum (E) was added in the master batch obtained and kneaded until it became uniform. After that, 0.2 parts by weight of the organohydrogen polysiloxane (B) was added, and kneaded. Thereby a silicone rubber-based hardening composition was prepared.

The weight ratio of the raw material used is shown in Table 1.

(Evaluation of Silicone Rubber-Based Hardening Composition)

<Tear Strength and Tear Stroke>

The prepared silicone rubber-based hardening composition was pressed at 170° C. for 10 minutes with 10 MPa to mold a sheet having a thickness of 1 mm, and primarily hardened.

Then, the obtained sheet was heated at 200° C. for 4 hours, and secondarily hardened.

A crescent-shaped test piece was produced based on JIS K 6252 (2001) using the obtained silicone rubber in a sheet shape. Then, the tear strength and the elongation (stroke) until breaking of the crescent-shaped test piece were measured according to JIS K 6252 (2001). Moreover, the thickness of the test piece was 1 mm. The results are shown in Table 1.

<Tensile Strength and Tensile Elongation Rate>

The prepared silicone rubber-based hardening composition was pressed at 170° C. for 10 minutes with 10 MPa to mold a sheet having a thickness of 1 mm, and primarily hardened.

Then, the obtained sheet was heated at 200° C. for 4 hours, and secondarily hardened.

A dumb-bell shaped third test piece was produced based on JIS K 6251 (2004) using the obtained silicone rubber in a sheet shape. Then, the tensile strength and the elongation (strain) at break of the dumb-bell shaped third test piece were measured according to JIS K 6251 (2004). Moreover, the thickness of the test piece was 1 mm. The results are shown in Table 1.

TABLE 1

|  |  | Examples | | | | | Comparative Examples | | | |
|---|---|---|---|---|---|---|---|---|---|---|
|  |  | 1 | 2 | 3 | 4 | 5 | 1 | 2 | 3 | 4 |
| (A1) |  | 100.0 | 100.0 | 80.0 | 100.0 | 80.0 | 100.0 | 100.0 | 100.0 | 100.0 |
| (A2) |  | — | — | 20.0 | — | 20.0 | — | — | — | — |
| (B) |  | 2.0 | 2.0 | 2.0 | 2.0 | 2.0 | 2.0 | 2.0 | 2.0 | 2.0 |
| (C1) | 200 m$^2$/g(*1) 12 nm(*2) | 50 | 70 | 70 | — | — | — | — | — | — |
| (C2) | 300 m$^2$/g(*1) 7 nm(*2) | — | — | — | 70 | 70 | — | — | — | — |
| (c1) | 200 m$^2$/g(*1) 12 nm(*2) | — | — | — | — | — | 33 | — | — | — |
| (c2) | 130 m$^2$/g(*1) 16 nm(*2) | — | — | — | — | — | — | 50 | — | — |
| (c3) | 200 m$^2$/g(*1) 12 nm(*2) | — | — | — | — | — | — | — | 50 | 70 |
| (D) |  | 0.5 | 0.5 | 0.5 | 0.5 | 0.5 | 0.5 | 0.5 | 0.5 | 0.5 |
| JIS K6252 | Tear strength (N/mm) | 28.3 | 36.3 | 40.3 | 48.0 | 50.2 | 13.7 | 10.9 | 21.3 | 12.4 |
|  | Stroke (mm) | 180.1 | 142.4 | 182.8 | 194.6 | 225.8 | 15.0 | 23.3 | 43.5 | 6.4 |

TABLE 1-continued

|  |  | Examples | | | | | Comparative Examples | | | |
| --- | --- | --- | --- | --- | --- | --- | --- | --- | --- | --- |
|  |  | 1 | 2 | 3 | 4 | 5 | 1 | 2 | 3 | 4 |
| JIS K6251 | Tensile strength (MPa) | 9.2 | 8.2 | 7.6 | 10.2 | 8.6 | 5.1 | 9.2 | 10.3 | 8.4 |
|  | Elongation at breaking (%) | 1662.4 | 1255.1 | 1375.6 | 1460.3 | 1389.5 | 572.8 | 827.3 | 993.3 | 474.9 |

(*1)Specific surface area of silica filler
(*2)Primarily particle diameter of silica filler Example 2

The silicone rubber-based hardening composition was obtained in a manner identical to that of Example 1, except that the content of the silica filler (C) was changed to 7.0 parts by weight.

In addition, evaluation of a test piece which was produced using the obtained silicone rubber-based hardening composition was carried out in a manner identical to that of Example 1. The results are shown in Table 1.

Example 3

Preparation of Silicone Rubber-Based Hardening Composition 80 parts by weight of the first linear organopolysiloxane containing a vinyl group (A1) and 20 parts by weight of the second linear organopolysiloxane containing a vinyl group were mixed in advance. Then, 70 parts by weight of the silica filler (C1) was added in the mixture, and kneaded. Thereby, a master batch was obtained.

Then, 0.5 parts by weight of platinum (E) was in the master batch obtained and kneaded until it became uniform. After that, 0.2 parts by weight of the organohydrogen polysiloxane (B) was added, and kneaded. Thereby a silicone rubber-based hardening composition was prepared.

(Evaluation of Silicone Rubber-Based Hardening Composition)

A test piece which was obtained by using the obtained silicone rubber-based hardening composition was evaluated similar to Example 1. The results are shown in Table 1.

Example 4

The silicone rubber-based hardening composition was obtained in a manner identical to that of Example 2, except that the silica filler (C2) was used instead of the silica filler (C1).

In addition, evaluation of a test piece which was produced using the obtained silicone rubber-based hardening composition was carried out in a manner identical to that of Example 1. The results are shown in Table 1.

Example 5

The silicone rubber-based hardening composition was obtained in a manner identical to that of Example 3, except that the silica filler (C2) was used instead of the silica filler (C1).

In addition, evaluation of a test piece which was produced using the obtained silicone rubber-based hardening composition was carried out in a manner identical to that of Example 1. The results are shown in Table 1.

Comparative Example 1

The silicone rubber-based hardening composition was obtained in a manner identical to that of Example 1, except that 33 parts by weight of the silica filler (c1) was used instead of 50 parts by weight of the silica filler (C1).

In addition, evaluation of a test piece which was produced using the obtained silicone rubber-based hardening composition was carried out in a manner identical to that of Example 1. The results are shown in Table 1.

Comparative Example 2

The silicone rubber-based hardening composition was obtained in a manner identical to that of Example 1, except that the content of the silica filler (c2) was used instead of the silica filler (C1).

In addition, evaluation of a test piece which was produced using the obtained silicone rubber-based hardening composition was carried out in a manner identical to that of Example 1. The results are shown in Table 1.

Comparative Example 3

The silicone rubber-based hardening composition was obtained in a manner identical to that of Example 1, except that the content of the silica filler (c3) was used instead of the silica filler (C1).

In addition, evaluation of a test piece which was produced using the obtained silicone rubber-based hardening composition was carried out in a manner identical to that of Example 1. The results are shown in Table 1.

Comparative Example 4

The silicone rubber-based hardening composition was obtained in a manner identical to that of Example 1, except that 70 parts by weight of the silica filler (c3) was used instead of 50 parts by weight of the silica filler (C1).

In addition, evaluation of a test piece which was produced using the obtained silicone rubber-based hardening composition was carried out in a manner identical to that of Example 1. The results are shown in Table 1.

Additional Examples 1 to 4

The silicone rubber-based hardening compositions were obtained in a manner identical to that of Example 4, except that the contents of the organohydrogen polysiloxane (B) and/or the silica filler (C2) were changed to various amounts shown in Table 1-2.

In addition, evaluation of test pieces which were produced using the obtained silicone rubber-based hardening compositions was carried out in a manner identical to that of Example 1. The results are shown in Table 1-2.

TABLE 1-2

| | | Additional Examples | | | |
|---|---|---|---|---|---|
| | | 1 | 2 | 3 | 4 |
| | (A1) | 80.0 | 80.0 | 80.0 | 80.0 |
| | (A2) | 20.0 | 20.0 | 20.0 | 20.0 |
| | (B) | 3.0 | 2.5 | 2.0 | 3.0 |
| (C1) | 200 m$^2$/g(*1) 12 nm(*2) | 70 | — | — | — |
| (C2) | 300 m$^2$/g(*1) 7 nm(*2) | — | 70 | 56 | 56 |
| (c1) | 200 m$^2$/g(*1) 12 nm(*2) | — | — | — | — |
| (c2) | 130 m$^2$/g(1*) 16 nm(*2) | — | — | — | — |
| (c3) | 200 m$^2$/g(*1) 12 nm(*2) | — | — | — | — |
| | (D) | 0.5 | 0.5 | 0.5 | 0.5 |
| JIS K6252 | Tear strength (N/mm) | 43.4 | 41.4 | 46.9 | 45.6 |
| | Stroke (mm) | 95.1 | 131.9 | 295.1 | 164.7 |
| JIS K6251 | Tensile strength (MPa) | 8.3 | 8.0 | 8.0 | 9.2 |
| | Elongation at breaking (%) | 947.8 | 1108.2 | 1691.6 | 1193.6 |

(*1)Specific surface area of silica filler
(*2)Primarily particle diameter of silica filler

[Results]

As shown in Table 1 and Table 1-2, the silicone rubber which is obtained by hardening the silicone rubber-based hardening composition containing the silica filler (C1) or (C2) of which the surface is treated with the silane coupling agent having a trimethylsilyl group has 28 N/nn or more of the tear strength, and 7.5 MPa or more of tensile strength. The silicone rubber is excellent in the tear strength and the tensile strength. In particular, the tear strength of the silicone rubber obtained in Examples 1 to 5 is remarkably improved compared with the tear strength of the silicone rubber obtained in Comparative Examples 1 to 4 which contains the silica filler (c1) to (c3) of which the surface is not treated with the silane coupling agent having a trimethylsilyl group. In addition, the stroke and the elongation at breaking of the silicone rubber in Examples 1 to 5 are remarkably improved compared with those of the silicone rubber in Comparative Examples 1 to 4. Thereby, it was confirmed that the silicone rubber in Examples 1 to 5 had high elongation even when containing a large amount of the silica filler.

Next, it can be understood by the comparison between Examples 1 and 2 that when the content of the silica filler (C1) (trimethylsiliyl group-surface treated silica filler (C)) is increased, the tear strength of the silicone rubber is increased. In contrast, it can be understood by the comparison between Comparative Examples 3 and 4 that when the content of the silica filler (c3) is increased, the tear strength of the silicone rubber is remarkably decreased. The reason for the large decrease of tear strength is considered to be because the surface of the silica filler (c3) is treated with dimethyldichlorosilane, and therefore, the silica filler (c3) has higher cohesive force compared with the silica filler (C) of which the surface is treated with the silane coupling agent having a trimethylsilyl group. When a large amount of the silica filler (c3) is added, the elongation of the silicone rubber is remarkably decreased, and because of this, the silicone rubber easily reaches a breaking point, and the tear strength is decreased. In contrast, the surface of the silica filler (C1) used in Examples is treated with the silane coupling agent having a trimethylsilyl group, and therefore the silica filler has lower cohesive force. As a result, the molecular chains of the silicone rubber easily slip. Therefore, even when a large amount of the silica filler is added, the decrease of elongation of the silicone rubber is small. Due to this, sufficient stiffening effects due to the silica filler can be obtained.

In addition, it can be understood by the comparison between Examples 2 and 4, and the comparison between Examples 3 and 5 that when the specific surface area of the silica filler (C1) or (C2) (trimethylsiliyl group-surface treated silica filler (C)) is increased, not only the tear strength but also the stroke, tensile strength, and the elongation at breaking are also improved. The reason for the improvement is considered to be because the interface between the silica filler and the rubber matrix is increased by increase of the specific surface area of the silica filler. Due to this, sufficient stiffening effects due to the silica filler can be obtained. At the same time, it can be understood by the comparison between Examples 2 and 4, and the comparison between Examples 3 and 5 that when the primarily particle diameter of the silica filler (C1) or (C2) (trimethylsiliyl group-surface treated silica filler (C)) is increased, not only the tear strength but also the stroke, tensile strength, and the elongation at breaking are also improved.

In addition, it can be understood by the comparison between Examples 2 and 3, and the comparison between Examples 4 and 5 that the tear strength, stroke, and elongation at breaking are improved by using the first linear organopolysiloxane containing a vinyl group (A1) and the second first linear organopolysiloxane containing a vinyl group (A2) as the linear organopolysiloxane containing a vinyl group (A) compared with the case of using only the first linear organopolysiloxane containing a vinyl group (A1).

The following materials were used in Examples 6 to 8, Comparative Examples 5 to 8, and Additional Examples 5 and 6.

(A1): first linear organopolysiloxane containing a vinyl group, the content of a vinyl group: 0.13% by mole, and this was synthesized by the following synthesis scheme.

(A2): second linear organopolysiloxane containing a vinyl group, the content of a vinyl group: 0.92% by mole, and this was synthesized by the following synthesis scheme.

(B): organohydrogen polysiloxane made by Momentive Inc. trade name: TC-25D (C1): silica filler of which the surface is treated with hexamethyldisilazane made of Nippon Aerosil Co., Ltd., trade name: Aerosil® RX200, specific surface area: 200 m$^2$/g; average primary particle diameter: 12 nm; and carbon content: 2.5% by weight (C2): silica filler of which the surface is treated with hexamethyldisilazane made of Nippon Aerosil Co., Ltd., trade name: Aerosil® RX300, specific surface area: 300 m$^2$/g; average primary particle diameter: 7 nm; and carbon content: 3.5% by weight (D1): silica filler of which the surface is treated with methacryloxypropyltriethoxysilane, made of Nippon Aerosil Co., Ltd., trade name: Aerosil® R711, specific surface area: 200 m$^2$/g; and average primary particle diameter: 12 nm (D2): silica filler of which the surface is treated with methacryloxypropyltriethoxysilane, specific surface area: 300 m$^2$/g; and average primary particle diameter: 7 nm (E) platinum made by Momentive Inc. trade name: TC-25A (f) silica filler of which the surface is treated with dimethyldichlorosilane, made of Nippon Aerosil Co., Ltd., trade name: Aerosil® R974, specific surface area: 200 m²/g; and average primary particle diameter: 12 nm

[Synthesis of First Linear Organopolysiloxane Containing a Vinyl Group (A1)]

Based on the following formula (3), the first linear organopolysiloxane containing a vinyl group (A1) was synthesized.

Specifically, 74.7 g (252 mmol) of octamethylcyclotetrasiloxana, 0.086 g (0.25 mmol) of 2,4,6,8-tetramethyl 2,4,6,8-tetravinylcyclotetrasiloxane, and 0.1 g of potassium siliconate were put into a 300 mL-separable flask provided with a cooling pipe, and an impeller, of which the inside was replaced with Ar gas. Then, the temperature was raised, and the mixture was stirred at 120° C. for 30 minutes. After that, raising of the viscosity of the mixture was confirmed.

Then, the temperature was further increased to 155° C., and stirred for 3 hours. After 3 hours, 0.1 g (0.6 mmol) of 1,3-divinyltetramethyldisiloxane was added, and the mixture was stirred at 155° C. for 4 hours.

After 4 hours, the product was diluted with 250 mL of toluene, and washed with water 3 times. After washing, the organic phase was reprecipitated by washing with 1.5 L of methanol several times and purified to separate an oligomer and a polymer. The obtained polymer was dried at 60° C. under reduced pressure overnight, and the first linear organopolysiloxane containing a vinyl group (A1) (Mn: 277, 734; Mw: 573, 906; IV value (dl/g): 0.89) was produced.

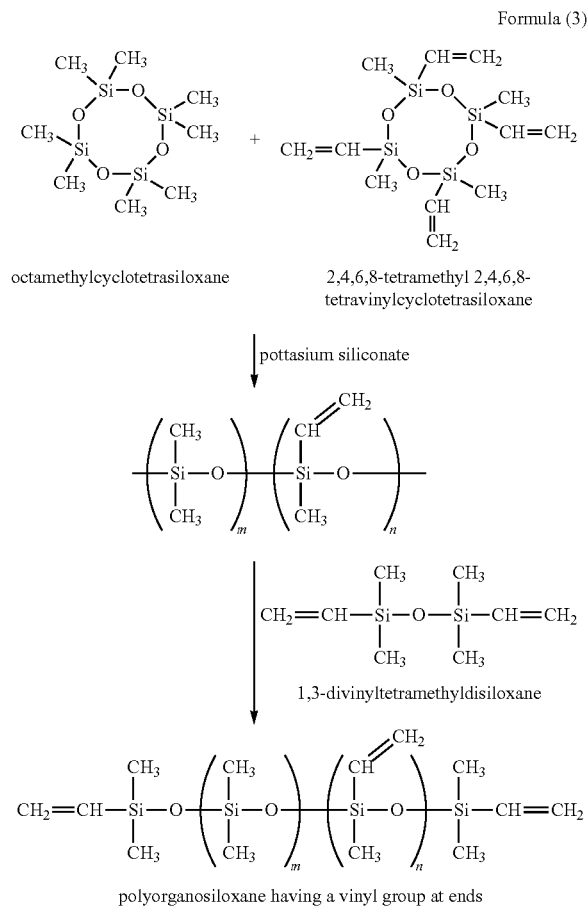

Formula (3)

[Synthesis of Second Linear Organopolysiloxane Containing a Vinyl Group (A2)]

The second linear organopolysiloxane containing a vinyl group (A2) was synthesized in a manner identical to that of the first linear organopolysiloxane containing a vinyl group (A1) except that 0.86 g (2.5 mmol) of 2,4,6,8-tetramethyl 2,4,6,8-tetravinylcyclotetrasiloxane was used.

Example 6

Preparation of Silicone Rubber-Based Hardening Composition 80 parts by weight of the first linear organopolysiloxane containing a vinyl group (A1) and 20 parts by weight of the second linear organopolysiloxane containing a vinyl group were mixed in advance. Then, 64.3 parts by weight of the silica filler (C1) and 5.4 parts by weight of the silica filler (D1) were added in the mixture, and kneaded. Thereby, a master batch was obtained.

Then, 0.5 parts by weight of platinum (E) was in the master batch obtained and kneaded until it became uniform. After that, 0.2 parts by weight of the organohydrogen polysiloxane (B) was added, and kneaded. Thereby a silicone rubber-based hardening composition was prepared.

The weight ratio of the raw materials used is shown in Table 2.

(Evaluation of Silicone Rubber-Based Hardening Composition)

<Tear Strength and Tear Stroke>

The prepared silicone rubber-based hardening composition was pressed at 170° C. for 10 minutes with 10 MPa to mold a sheet having a thickness of 1 mm, and primarily hardened.

Then, the obtained sheet was heated at 200° C. for 4 hours, and secondarily hardened.

A crescent-shaped test piece was produced based on JIS K 6252 (2001) using the obtained silicone rubber in a sheet shape. Then, the tear strength and the elongation (stroke) until breaking of a crescent-shaped test piece were measured according to JIS K 6252 (2001). Moreover, the thickness of the test piece was 1 mm. The results are shown in Table 2.

<Tensile Strength and Tensile Elongation Rate>

The prepared silicone rubber-based hardening composition was pressed at 170° C. for 10 minutes with 10 MPa to mold a sheet having a thickness of 1 mm, and primarily hardened.

Then, the obtained sheet was heated at 200° C. for 4 hours, and secondarily hardened.

A dumb-bell shaped third test piece was produced using the obtained silicone rubber in a sheet shape according to JIS K 6251 (2004). Then, the tensile strength and the elongation (strain) until breaking of the dumb-bell shaped third test piece were measured according to JIS K 6251 (2004). Moreover, the thickness of the test piece was 1 mm. The results are shown in Table 2.

<Hardness>

The prepared silicone rubber-based hardening composition was pressed at 170° C. for 10 minutes with 10 MPa to mold a sheet having a thickness of 1 mm, and primarily hardened. Then, the obtained sheet was heated at 200° C. for 4 hours, and secondarily hardened.

Then, the type A durometer hardness of the silicone rubber in a sheet shape was measured based on JIS K 6253 (2006).

TABLE 2

|  |  | Examples | | | | | Comparative Examples | |
|---|---|---|---|---|---|---|---|---|
|  |  | 6 | 7 | 8 | 9 | 10 | 5 | 6 |
| (A1) |  | 80.0 | 100.0 | 100.0 | 80.0 | 100.0 | 100 | 100 |
| (A2) |  | 20.0 | — | — | 20.0 | — | — | — |
| (B) |  | 2.0 | 2.0 | 2.0 | 2.0 | 2.0 | 2.0 | 2.0 |
| (C1) | 200 m$^2$/g (*1) 12 nm (*2) | 64.3 | — | — | 70 | — | — | — |
| (C2) | 300 m$^2$/g (*1) 7 nm (*2) | — | 66 | 60 | — | 70 | — | — |
| (D1) | 200 m$^2$/g (*1) 12 nm (*2) | 5.4 | — | — | — | — | 70 | — |
| (D2) | 300 m$^2$/g (*1) 7 nm (*2) | — | 4.2 | 9.0 | — | — | — | — |
| (f) | 200 m$^2$/g (*1) 12 nm (*2) | — | — | — | — | — | — | 70 |
| (E) |  | 0.5 | 0.5 | 0.5 | 0.5 | 0.5 | 0.5 | 0.5 |
| JIS K6252 | Tear strength (N/mm) stroke (mm) | 38.3 170.0 | 42.8 156.2 | 42.2 249.4 | 40.3 182.8 | 41.5 207.6 | 11.3 6.6 | 12.4 6.4 |
| JIS K6251 | Tensile strength (MPa) Elongation at breaking (%) | 7.2 1299.9 | 7.1 926.9 | 6.8 1043.6 | 7.6 1375.6 | 6.9 1008.2 | 2.2 131.2 | 8.4 474.9 |
| JIS K6253 | Type A durometer hardness (shoreA) | 58.7 | 61.8 | 63.0 | 49.3 | 54.0 | 74.7 | 80.2 |

(*1): Specific surface area of silica filler
(*2): Primarily particle diameter of silica filler

Example 7

66 parts by weight of the silica filler (C2), and 4.2 parts by weight of the silica filler (D2) were added in 100 parts by weight of the first linear organopolysiloxane having a vinyl group (A1), and kneaded to prepare a master batch.

Then, 0.5 parts by weight of platinum (E) was in the master batch obtained and kneaded until it became uniform. After that, 0.2 parts by weight of the organohydrogen polysiloxane (B) was added, and kneaded. Thereby a silicone rubber-based hardening composition was prepared.

Similar to Example, 6, the test piece was produced using the obtained silicone rubber-based hardening composition, and evaluated. The results are shown in Table 2.

Example 8

The silicone rubber-based hardening composition was obtained in a manner identical to that of Example 7, except that the content of the silica filler (C1) and the silica filler (D2) was changed to 60 parts by weight and 9 parts by weight respectively.

Similar to Example, 6, the test piece was produced using the obtained silicone rubber-based hardening composition, and evaluated. The results are shown in Table 2.

Example 9

The silicone rubber-based hardening composition was obtained in a manner identical to that of Example 6, except that 70 parts by weight of the silica filler (C1) was used instead of 64.3 parts by weight of the silica filler (C1) and 5.4 parts by weight of the silica filler (D1).

Similar to Example, 6, the test piece was produced using the obtained silicone rubber-based hardening composition, and evaluated. The results are shown in Table 2.

Example 10

The silicone rubber-based hardening composition was obtained in a manner identical to that of Example 7, except that 70 parts by weight of the silica filler (C2) was used instead of 66 parts by weight of the silica filler (C2) and 4.2 parts by weight of the silica filler (D2).

Similar to Example, 6, the test piece was produced using the obtained silicone rubber-based hardening composition, and evaluated. The results are shown in Table 2.

Comparative Example 5

The silicone rubber-based hardening composition was obtained in a manner identical to that of Example 10, except that the silica filler (D1) was used instead of the silica filler (C2).

Similar to Example 6, the test piece was produced using the obtained silicone rubber-based hardening composition, and evaluated. The results are shown in Table 2.

Comparative Example 6

The silicone rubber-based hardening composition was obtained in a manner identical to that of Example 10, except that the silica filler (f) was used instead of the silica filler (C2).

Similar to Example 6, the test piece was produced using the obtained silicone rubber-based hardening composition, and evaluated. The results are shown in Table 2.

Additional Examples 5 and 6

The silicone rubber-based hardening compositions were obtained in a manner identical to that of Example 6, except that the contents of the organohydrogen polysiloxane (B), the silica filler (C1), and/or the silica filler (D1) were changed to various amounts shown in Table 2-2.

Similarly to Example 6, the test pieces were produced using the obtained silicone rubber-based hardening compositions, and evaluated. The results are shown in Table 2-2.

TABLE 2-2

| | | Additional Examples ||
| | | 5 | 6 |
|---|---|---|---|
| | (A1) | 80.0 | 80.0 |
| | (A2) | 20.0 | 20.0 |
| | (B) | 3.0 | 2.0 |
| (C1) | 200 m²/g (*1) 12 nm (*2) | 64.3 | 37.1 |
| (C2) | 300 m²/g (*1) 7 nm (*2) | — | — |
| (D1) | 200 m²/g (*1) 12 nm (*2) | 5.4 | 2.9 |
| (D2) | 300 m²/g (*1) 7 nm (*2) | — | — |
| (f) | 200 m²/g (*1) 12 nm (*2) | — | — |
| | (E) | 0.5 | 0.5 |
| JIS K6252 | Tear strength (N/mm) | 34.6 | 37.3 |
| | Stroke (mm) | 87.6 | 283.7 |
| JIS K6251 | Tensile strength (MPa) | 8.6 | 9.1 |
| | Elongation at breaking (%) | 1006.1 | 2054.1 |
| JIS K6253 | Type A durometer hardness (shoreA) | 63.5 | 39.3 |

(*1): Specific surface area of silica filler
(*2): Primarily particle diameter of silica filler

[Results]

As shown in Table 2 and Table 2-2, the silicone rubber which is obtained by hardening the silicone rubber-based hardening composition containing the silica filler (C1) or (C2), and the silica filler (D1) or (D2) is excellent in the balance between the tear strength, tensile strength, and hardness compared with the silicone rubber in Examples 9 to 11 and Comparative Examples 5 and 6 which is obtained by hardening the silicone rubber-based hardening composition containing only the silica filler (C1), (C2), (D1), or (f).

Specifically, it can be understood by the comparison between Example 6 and Example 9, and comparison between Examples 7 and 8, and Example 10 that the silicone rubber in Examples 6 to 8 has improved hardness compared with the silicone rubber in Example 9 and 10 which contains only the silica filler (C1) or (C2).

In addition, it can be understood by the comparison between Examples 7 and 8 and Comparative Example 5 that the silicone rubber in Example 7 and 8 has remarkably improved tear strength and tensile strength in addition to the stroke and elongation at breaking, compared with the silicone rubber in Comparative Example 5 which contains only the silica filler (D1).

Furthermore, it is also understood by the comparison between Example 7 and 8 and Comparative Example 6 that the silicone rubber in Examples 7 and 8 has remarkably improved tear strength, stroke, and elongation at breaking compared with the silicone rubber in Comparative Example 6 which contains only the silica filler (f), and does not contain both of the silica fillers (C) and (D).

INDUSTRIAL APPLICABILITY

The silicone rubber obtained by hardening the silicone rubber-based hardening composition according to the present invention is excellent in mechanical strength such as tensile strength and tear strength, in particular, tear strength. Therefore, the molded article which is obtained by using the silicone rubber-based hardening composition and the medical tube which is obtained by using the molded article have high mechanical strength. In other words, according to the present invention, it is possible to produce a medical catheter made of silicone rubber which is excellent in scratch resistance and kink resistance, in particular, scratch resistance.

In other words, the present invention is extremely industrially important.

The invention claimed is:

1. A silicone rubber-based hardening composition, comprising:
    a linear organopolysiloxane comprising a vinyl group;
    an organohydrogen polysiloxane; and
    a silica filler of which surface is treated with a coupling agent comprising a trimethylsilyl group,
    wherein the linear organopolysiloxane comprising a vinyl group comprises a first linear organopolysiloxane comprising a vinyl group, and a second linear organopolysiloxane comprising a vinyl group, and each of the first linear organopolysiloxane comprising a vinyl group and the second linear organopolysiloxane comprising a vinyl group has a polymerization degree in a range of 4,000 to 8,000.

2. The silicone rubber-based hardening composition according to claim 1, wherein the first linear organopolysiloxane comprising a vinyl group comprises 0.2% by mole or less of a vinyl group, and the second linear organopolysiloxane comprising a vinyl group comprises 0.50% to 12% by mole of a vinyl group.

3. The silicone rubber-based hardening composition according to claim 1, wherein the first linear organopolysiloxane comprising a vinyl group comprises 0.01% to 0.2% by mole of a vinyl group, and the second linear organopolysiloxane comprising a vinyl group comprises 0.50% to 12% by mole of a vinyl group.

4. The silicone rubber-based hardening composition according to claim 1, wherein the first linear organopolysiloxane comprising a vinyl group and the second linear organopolysiloxane comprising a vinyl group are each represented by formula (1),

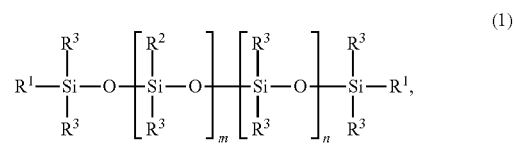

where, in formula (1), m denotes an integer from 1 to 1,000, n denotes an integer from 3,000 to 10,000, $R^1$ denotes a substituted or unsubstituted $C_{1-10}$ alkyl group, a substituted or unsubstituted $C_{2-10}$ alkenyl group, a substituted or unsubstituted $C_{6-10}$ aryl group, or a hydrocarbon group in which the substituted or unsubstituted $C_{1-10}$ alkyl group, the substituted or unsubstituted $C_{2-10}$ alkenyl group and the substituted or unsubstituted $C_{6-10}$ aryl group are combined, $R^2$ denotes a substituted or unsubstituted $C_{1-10}$ alkyl group, a substituted or unsubstituted $C_{2-10}$ alkenyl group, a substituted or unsubstituted $C_{6-10}$ aryl group, or a hydrocarbon group in which the substituted or unsubstituted $C_{1-10}$ alkyl group, the substituted or unsubstituted $C_{2-10}$ alkenyl group and the substituted or unsubstituted $C_{6-10}$ aryl group are combined, $R^3$ denotes a substituted or unsubstituted $C_{1-8}$ alkyl group, a substituted or unsubstituted $C_{6-8}$ aryl group, or a hydrocarbon group in which the substituted or unsubstituted $C_{1-8}$ alkyl group and the substituted or unsubstituted $C_{6-8}$ aryl group are combined, at least one of plural $R^1$ and $R^2$ is an alkenyl group, and the organohydrogen polysiloxane is a linear organohydrogen polysiloxane represented by formula (2),

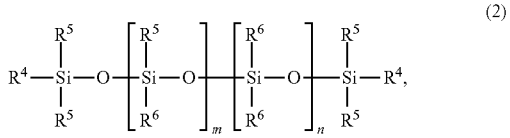

(2)

where, in formula (2), m denotes an integer from 2 to 500, n denotes an integer from 2 to 400, m and n satisfy $20 \leq (m+n) \leq 500$, $R^4$ denotes a substituted or unsubstituted $C_{1-10}$ alkyl group, a substituted or unsubstituted $C_{2-10}$ alkenyl group, a substituted or unsubstituted $C_{6-10}$ aryl group, a hydrocarbon group in which the substituted or unsubstituted $C_{1-10}$ alkyl group, the substituted or unsubstituted $C_{2-10}$ alkenyl group and the substituted or unsubstituted $C_{6-10}$ aryl group are combined, or a hydride group, $R^5$ denotes a substituted or unsubstituted $C_{1-10}$ alkyl group, a substituted or unsubstituted $C_{2-10}$ alkenyl group, a substituted or unsubstituted $C_{6-10}$ aryl group, a hydrocarbon group in which the substituted or unsubstituted $C_{1-10}$ alkyl group, the substituted or unsubstituted $C_{2-10}$ alkenyl group and the substituted or unsubstituted $C_{6-10}$ aryl group are combined, or a hydride group, at least two of plural $R^4$ and $R^5$ are a hydride group, and $R^6$ denotes a substituted or unsubstituted $C_{1-8}$ alkyl group, a substituted or unsubstituted $C_{6-8}$ aryl group, or a hydrocarbon group in which the substituted or unsubstituted $C_{1-8}$ alkyl group and the substituted or unsubstituted $C_{6-8}$ aryl group are combined.

5. The silicone rubber-based hardening composition according to claim 1, further comprising:
a silica filler of which surface is treated with a coupling agent comprising an organosilyl group comprising a vinyl group.

6. The silicone rubber-based hardening composition according to claim 1, wherein the organohydrogen polysiloxane is a linear organohydrogen polysiloxane represented by formula (2),

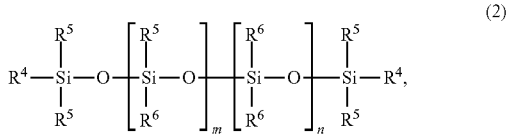

(2)

where, in formula (2), m denotes an integer from 2 to 500, n denotes an integer from 2 to 400, m and n satisfy $20 \leq (m+n) \leq 500$, $R^4$ denotes a substituted or unsubstituted $C_{1-10}$ alkyl group, a substituted or unsubstituted $C_{2-10}$ alkenyl group, a substituted or unsubstituted $C_{6-10}$ aryl group, a hydrocarbon group in which the substituted or unsubstituted $C_{1-10}$ alkyl group, the substituted or unsubstituted $C_{2-10}$ alkenyl group and the substituted or unsubstituted $C_{6-10}$ aryl group are combined, or a hydride group, $R^5$ denotes a substituted or unsubstituted $C_{1-10}$ alkyl group, a substituted or unsubstituted $C_{2-10}$ alkenyl group, a substituted or unsubstituted $C_{6-10}$ aryl group, a hydrocarbon group in which the substituted or unsubstituted $C_{1-10}$ alkyl group, the substituted or unsubstituted $C_{2-10}$ alkenyl group and the substituted or unsubstituted $C_{6-10}$ aryl group are combined, or a hydride group, at least two of plural $R^4$ and $R^5$ are a hydride group, and $R^6$ denotes a substituted or unsubstituted $C_{1-8}$ alkyl group, a substituted or unsubstituted $C_{6-8}$ aryl group, or a hydrocarbon group in which the substituted or unsubstituted $C_{1-8}$ alkyl group and the substituted or unsubstituted $C_{6-8}$ aryl group are combined.

7. The silicone rubber-based hardening composition according to claim 1, wherein the coupling agent comprising a trimethylsilyl group is at least one selected from the group consisting of silazane, chlorosilane, and alkoxysilane.

8. The silicone rubber-based hardening composition according to claim 1, wherein the coupling agent comprising a trimethylsilyl group is at least one selected from the group consisting of hexamethyldisilazane, trimethylchlorosilane, trimethylmethoxysilane, and trimethylethoxysilane.

9. The silicone rubber-based hardening composition according to claim 1, wherein the silica filler comprises carbon in a range of 0.1% to 7.0% by weight.

10. The silicone rubber-based hardening composition according to claim 1, wherein the silica filler has a specific surface area in a range of 30 to 500 m$^2$/g, and an average primary particle diameter of 100 nm or less.

11. The silicone rubber-based hardening composition according to claim 5, wherein the coupling agent comprising an organosilyl group comprising a vinyl group is at least one selected from the group consisting of silazane, chlorosilane, and alkoxysilane.

12. The silicone rubber-based hardening composition according to claim 5, wherein the coupling agent comprising an organosilyl group comprising a vinyl group is at least one selected from the group consisting of methacryloxypropyl triethoxysilane, methacryloxypropyl trimethoxysilane, methacryloxypropyl methyl diethoxysilane, methacryloxypropyl methyldimethoxysilane, divinyl tetramethyldisilazane, vinyltriethoxysilane, vinyltrimethoxysilane, and vinylmethyldimethoxysilane.

13. The silicone rubber-based hardening composition according to claim 2, wherein the silica filler has a specific surface area in a range of 30 to 500 m$^2$/g, and an average primary particle diameter of 100 nm or less.

14. The silicone rubber-based hardening composition according to claim 1, wherein the organohydrogen polysiloxane does not comprise a vinyl group.

15. The silicone rubber-based hardening composition according to claim 1, wherein the organohydrogen polysiloxane has an amount of 0.1 to 10 parts by weight, and the silica filler has an amount of 15 to 150 parts by weight, relative to 100 parts by weight of the linear organopolysiloxane comprising a vinyl group.

16. The silicone rubber-based hardening composition according to claim 5, wherein the organohydrogen polysiloxane has an amount of 0.1 to 10 parts by weight, the silica filler treated with a coupling agent comprising a trimethylsilyl group has an amount of 15 to 150 parts by weight, and the silica filler treated with a coupling agent comprising an organosilyl group has an amount of 0 to 40 parts by weight, relative to 100 parts by weight of the linear organopolysiloxane.

17. The silicone rubber-based hardening composition according to claim 1, further comprising:
a catalyst comprising platinum or a platinum compound in a catalyst quantity.

18. A molded article obtained by a process according molding the silicone rubber-based hardening composition according to claim 1.

19. A medical tube, comprising:
a molded article obtained by a process comprising molding the silicone rubber-based hardening composition according to claim 1.

20. The silicone rubber-based hardening composition according to claim 1, wherein the silica filler comprises carbon in a range of 0.1% to 7.0% by weight and has a specific surface area in a range of 30 to 500 $m^2/g$, and an average primary particle diameter of 100 nm or less.

* * * * *